(12) United States Patent
Yu et al.

(10) Patent No.: US 10,479,789 B2
(45) Date of Patent: Nov. 19, 2019

(54) PYRIDO[1,2-A]PYRIMIDONE ANALOG, CRYSTAL FORM THEREOF, INTERMEDIATE THEREOF AND PREPARATION METHOD THEREFOR

(71) Applicant: Chia Tai Tianqing Pharmaceutical Group Co., Ltd., Lianyungang, Jiangsu (CN)

(72) Inventors: Tao Yu, Shanghai (CN); Ning Li, Shanghai (CN); Lingwei Kong, Shanghai (CN); Peipei Jiang, Shanghai (CN); Yong Wang, Shanghai (CN); Zhemin Rong, Shanghai (CN); Changjun Wang, Shanghai (CN); Feng Guo, Shanghai (CN); Zongbin Li, Shanghai (CN); Zheng Wang, Shanghai (CN); Jiahu Wu, Shanghai (CN); Chengde Wu, Shanghai (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/061,279

(22) PCT Filed: Dec. 16, 2016

(86) PCT No.: PCT/CN2016/110284
§ 371 (c)(1),
(2) Date: Jun. 11, 2018

(87) PCT Pub. No.: WO2017/101847
PCT Pub. Date: Jun. 22, 2017

(65) Prior Publication Data
US 2018/0319799 A1    Nov. 8, 2018

(30) Foreign Application Priority Data
Dec. 16, 2015    (CN) ............. 2015 1 0951482

(51) Int. Cl.
*C07D 471/04*    (2006.01)
*A61K 31/519*    (2006.01)
*A61P 35/00*    (2006.01)

(52) U.S. Cl.
CPC .......... *C07D 471/04* (2013.01); *A61K 31/519* (2013.01); *A61P 35/00* (2018.01); *C07B 2200/13* (2013.01)

(58) Field of Classification Search
CPC .................................................. C07D 471/04
See application file for complete search history.

(56) References Cited

U.S. PATENT DOCUMENTS 9,856,256 B2 * 1/2018 Wu ................. A61K 31/519
2017/0137420 A1    5/2017 Wu

FOREIGN PATENT DOCUMENTS

| CN | 103539777 A | 1/2014 |
| CN | 105461711 A | 4/2016 |
| WO | WO 2014/022128 A1 | 2/2014 |
| WO | WO 2015/192760 A1 | 12/2015 |
| WO | WO2015192760 | * 12/2015 |

OTHER PUBLICATIONS

International Search Report in International Patent Application No. PCT/CN2016/110284, dated Mar. 23, 2017, 7 pages (w/English translation).
Written Opinion in International Patent Application No. PCT/CN2016/110284, dated Mar. 23, 2017, 20 pages (w/English translation).
Caira, M., "Crystalline Polymorphism of Organic Compounds," Department of Chemistry, University of Cape Town, Rondebosch 7700, South Africa, Topics in Current Chemistry, vol. 198, @Springer Verlag Berlin Heidelberg (1998), pp. 163-208 (46 pages).

* cited by examiner

*Primary Examiner* — Paul V Ward
(74) *Attorney, Agent, or Firm* — Nixon Peabody LLP

(57) ABSTRACT

Disclosed in the present invention are a crystalline Form of pyrido[1,2-a]pyrimidone analog, a preparation method therefor and an intermediate thereof.

17 Claims, 14 Drawing Sheets

Compound 1

Exothermic peak upwards

Exothermic peak upwards

Exothermic peak upwards

Exothermic peak upwards

Exothermic peak upwards

Exothermic peak upwards    Temperature (°C)

Exothermic peak upwards

Figure 1:
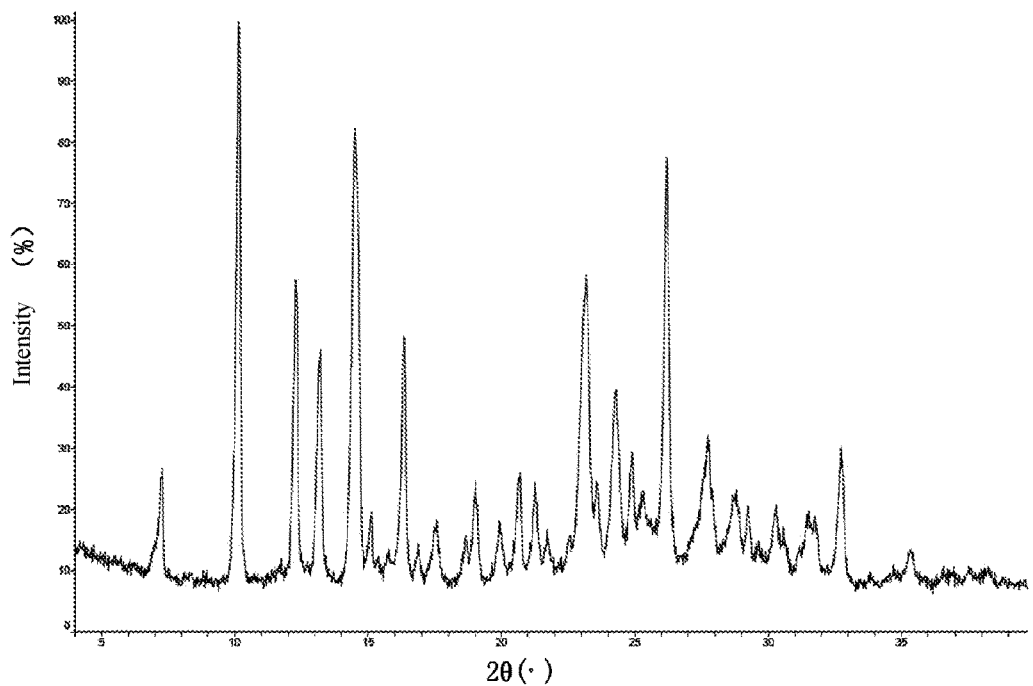

PYRIDO[1,2-A]PYRIMIDONE ANALOG, CRYSTAL FORM THEREOF, INTERMEDIATE THEREOF AND PREPARATION METHOD THEREFOR

CROSS-REFERENCE TO RELATED APPLICATIONS

The present application is a U.S. national stage of PCT/CN2016/110284 filed on Dec. 16, 2016, which claims the benefit of Chinese Patent Application No. 201510951482.3 filed on Dec. 16, 2015 in China.

FIELD OF THE INVENTION

The present invention relates to a crystal form of pyrido[1,2-a]pyrimidone analog, a preparation method therefor and an intermediate thereof.

BACKGROUND OF THE INVENTION

PI3K pathway is a site in human cancer cells where mutations most commonly occur and can lead to cell proliferation, activation, and signal amplification.

PI3K kinase (phosphatidylinositol-3-kinase, PI3Ks) belongs to the family of lipid kinases and can phosphorylate the 3'-OH terminus of the inositol ring of phosphatidylinositol. PI3K is a lipid kinase composed of a regulatory subunit p85 or p101 and a catalytic subunit p110, and plays a key role in cell proliferation, survival and metabolism etc. by catalyzing phosphorylation of phosphatidylinositol 4,5-bisphosphate (PIP2) to form phosphatidylinositol 3,4,5-trisphosphate (PIP3), thereby activating the downstream Akt and the like. Therefore, the inhibition of phosphatidylinositol-3-kinase may affect the PI3K pathway, and thus inhibit the proliferation and activation of cancer cells.

Tumor suppressor gene PTEN (Phosphatase and tension homolog deleted on chromosome ten) dephosphorylates PIP3 to generate PIP2, thus achieving negative regulation of the PI3K/Akt signaling pathway, inhibiting cell proliferation and promoting apoptosis. The frequent occurrence of PI3K gene mutation and amplification as well as the loss of PTEN in cancer and the like indicate that PI3K is closely relayed to tumorigenesis.

SUMMARY OF THE INVENTION

The present invention provides a method for preparing Compound 1,

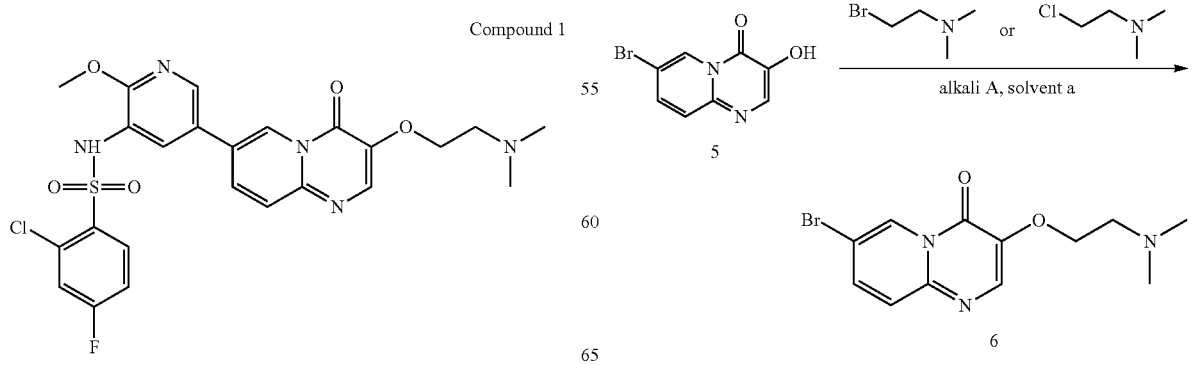

Compound 1 which comprises the following steps:

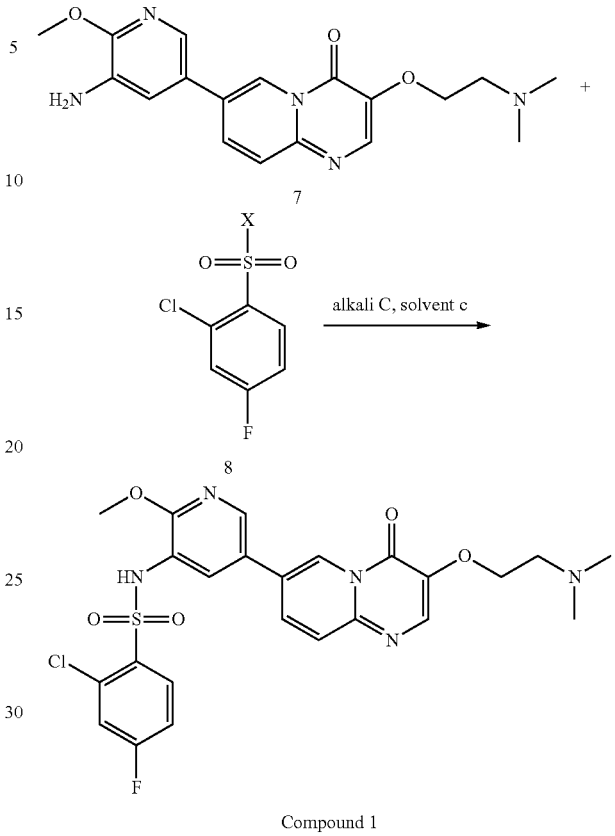

Compound 1 wherein
X is selected from Cl or Br;
alkali C is selected from pyridine, 2,6-lutidine, Et$_3$N, 4-DMAP, LiOH, Cs$_2$CO$_3$, or K$_2$CO$_3$;
solvent c is selected from pyridine, dichloromethane, toluene, acetonitrile, acetone, DMF or THF;
a molar ratio of Compound 7 to Compound 8 is 1:1~3;
a molar ratio of Compound 7 to alkali C is 1:1~3.

In some embodiments of the present invention, the molar ratio of Compound 7 to Compound 8 is 1:1.2~1.6.

In some embodiments of the present invention, the preparation of said Compound 1 comprises the following steps:

wherein
alkali A is selected from potassium carbonate, sodium carbonate, cesium carbonate, potassium hydroxide, or sodium hydroxide;
solvent a is selected from DMF, DMSO, or NMP.

Herein, 2-dimethylaminoethyl chloride or 2-dimethylaminoethyl bromide can be used in the form of a salt thereof, such as 2-dimethylaminoethyl chloride hydrochloride or 2-dimethylaminoethyl bromide hydrochloride.

In some embodiments of the present invention, a molar ratio of Compound 5 to 2-dimethylaminoethyl chloride (or its hydrochloride salt) or 2-dimethylaminoethyl bromide (or its hydrochloride salt) is 1:1~2.

In some embodiments of the present invention, the molar ratio of Compound 5 to 2-dimethylaminoethyl chloride (or its hydrochloride salt) or 2-dimethylaminoethyl bromide (or its hydrochloride salt) is 1:1.1~1.3.

In some embodiments of the present invention, the preparation of said Compound 1 comprises the following steps:

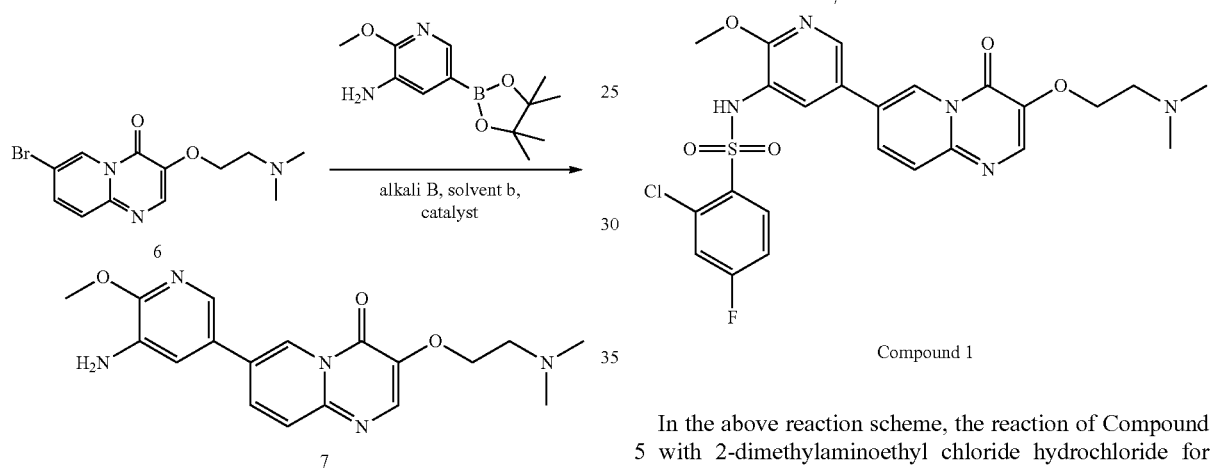

wherein
alkali B is selected from potassium carbonate, sodium carbonate, barium hydroxide, potassium phosphate, cesium carbonate, potassium fluoride, cesium fluoride, sodium hydroxide, potassium t-butoxide, sodium t-butoxide, potassium acetate or sodium acetate;
solvent b is selected from 1,4-dioxane, DMSO, THF, 1,4-dioxane/water, or THF/water;
a volume ratio of 1,4-dioxane or THF to water in solvent b is 3~6:1, preferably 5:1;
a catalyst is selected from Pd(dppf)Cl$_2$ or Pd(PPh$_3$)$_4$.

In some embodiments of the present invention, the volume ratio of 1,4-dioxane or THF to water in said solvent b is 5:1.

In some embodiments of the present invention, the preparation of said Compound 1 comprises the following steps:

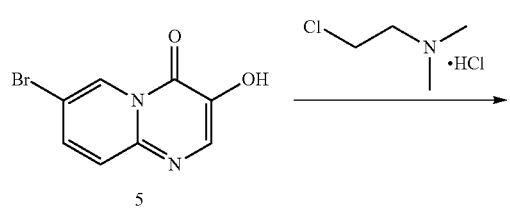

In the above reaction scheme, the reaction of Compound 5 with 2-dimethylaminoethyl chloride hydrochloride for generating Compound 6 is preferably performed in the presence of alkali A and solvent a, wherein alkali A is selected from potassium carbonate, sodium carbonate, cesium carbonate, potassium hydroxide or sodium hydroxide; and solvent a is selected from DMF, DMSO or NMP. In some embodiments of the present invention, the molar ratio of Compound 5 to 2-dimethylaminoethyl chloride hydrochloride is 1:1~2. In some embodiments of the present invention, the molar ratio of Compound 5 to 2-dimethylaminoethyl chloride hydrochloride is 1:1.1~1.3.

In the above reaction scheme, the reaction of Compound 6 with 2-methoxy-5-(4,4,5,5-tetramethyl-1,3,2-dioxaborolan-2-yl)pyridine-3-amine for generating Compound 7 is preferably performed in the presence of alkali B, solvent b and a catalyst, wherein alkali B is selected from potassium carbonate, sodium carbonate, barium hydroxide, potassium phosphate, cesium carbonate, potassium fluoride, cesium fluoride, sodium hydroxide, potassium t-butoxide, sodium t-butoxide, potassium acetate or sodium acetate; solvent b is selected from 1,4-dioxane, DMSO, THF, 1,4-dioxane/water, or THF/water, wherein the volume ratio of 1,4-dioxane or THF to water in solvent b is 3~6:1, preferably 5:1; and the catalyst is selected from Pd(dppf)Cl$_2$ or Pd(PPh$_3$)$_4$.

In the above reaction scheme, the reaction of Compound 7 with 2-chloro-4-fluorobenzenesulfonyl chloride for generating Compound 1 is preferably performed in the presence of alkali C and solvent c, wherein alkali C is selected from pyridine, 2,6-lutidine, Et$_3$N, 4-DMAP, LiOH, Cs$_2$CO$_3$, or K₂CO₃; solvent c is selected from pyridine, dichloromethane, toluene, acetonitrile, acetone, DMF or THF; and the molar ratio of Compound 7 to 2-chloro-4-fluorobenzenesulfonyl chloride is 1:1~3; and the molar ratio of Compound 7 to alkali C is 1:1~3. In some embodiments of the present invention, the molar ratio of Compound 7 to 2-chloro-4-fluorobenzenesulfonyl chloride is 1:1.2~1.6.

The present invention also provides compounds represented by the following formulas as intermediates for preparation of Compound 1:

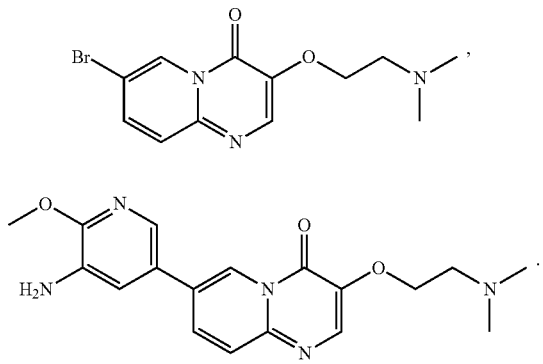

6

7

The present invention provides crystalline Form IX of Compound 1, characterized by having diffraction peaks at 2θ=7.947°, 10.073°, 14.531°, 19.187°, 21.237°, 24.055°, 25.497°; typically at 2θ=7.947°, 10.073°, 11.970°, 13.468°, 14.531°, 15.911°, 19.187°, 21.237°, 24.055°, 25.497°; more typically at 2θ=7.947°, 10.073°, 11.970°, 13.468°, 14.531°, 15.911°, 19.187°, 19.561°, 21.237°, 23.446°, 24.055°, 25.497°, 27.074°, in a X-ray diffraction (XRD) pattern.

Figure 25:
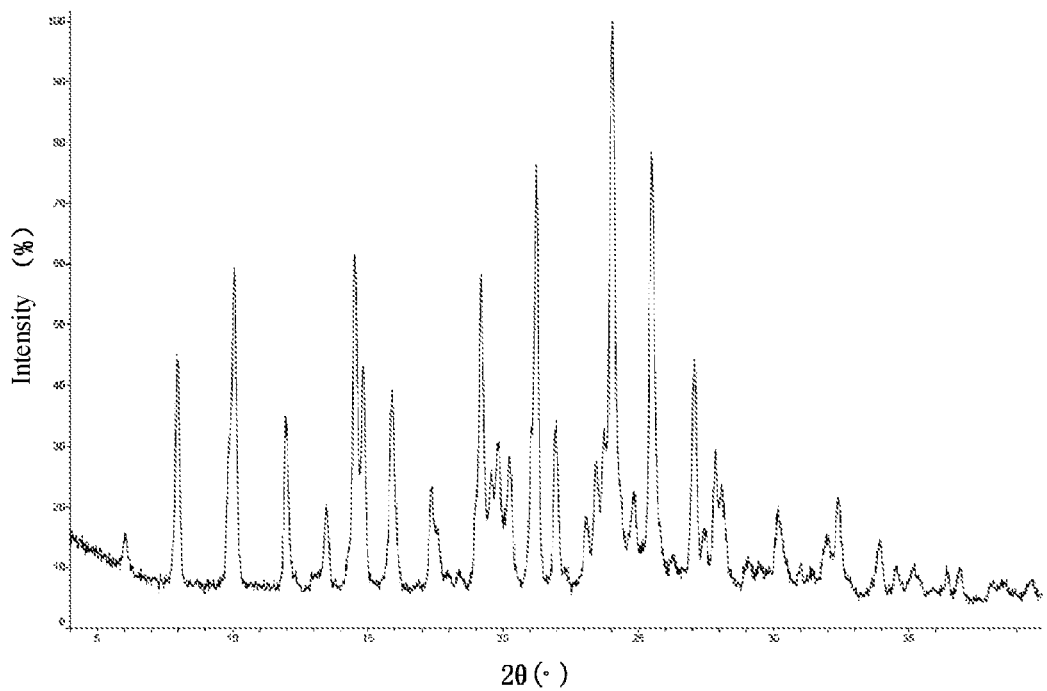

The present invention provides crystalline Form IX of Compound 1, which has a XRPD pattern as shown in FIG. 25.

In some embodiments of the present invention, XRPD pattern analysis data of said crystalline Form IX of Compound 1 is shown in Table 1.

TABLE 1

XRPD pattern analysis data of crystalline Form IX of Compound 1

| Nos. | 2θ degree | Relative intensity % | Nos. | 2θ degree | Relative intensity % |
|---|---|---|---|---|---|
| 1 | 6.014 | 2.5 | 24 | 24.847 | 6.6 |
| 2 | 7.947 | 29.0 | 25 | 25.497 | 60.4 |
| 3 | 10.073 | 54.2 | 26 | 26.265 | 1.3 |
| 4 | 11.970 | 23.3 | 27 | 27.074 | 28.0 |
| 5 | 13.053 | 5.9 | 28 | 27.448 | 10.1 |
| 6 | 13.468 | 14.4 | 29 | 27.862 | 22.8 |
| 7 | 14.531 | 62.5 | 30 | 28.081 | 15.6 |
| 8 | 14.828 | 49.7 | 31 | 29.005 | 4.5 |
| 9 | 15.911 | 31.1 | 32 | 29.445 | 3.3 |
| 10 | 17.369 | 21.8 | 33 | 30.171 | 13.0 |
| 11 | 17.569 | 26.1 | 34 | 31.014 | 1.5 |
| 12 | 17.941 | 4.5 | 35 | 31.437 | 0.7 |
| 13 | 18.377 | 1.6 | 36 | 31.963 | 19.5 |
| 14 | 19.187 | 55.2 | 37 | 32.381 | 23.5 |
| 15 | 19.561 | 41.3 | 38 | 33.937 | 9.1 |
| 16 | 19.855 | 61.5 | 39 | 34.565 | 4.7 |
| 17 | 20.233 | 22.2 | 40 | 35.218 | 6.8 |
| 18 | 21.237 | 62.8 | 41 | 36.403 | 5.8 |
| 19 | 21.984 | 22.0 | 42 | 36.897 | 3.7 |
| 20 | 22.373 | 3.2 | 43 | 38.103 | 7.1 |
| 21 | 23.073 | 2.2 | 44 | 38.605 | 6.8 |

TABLE 1-continued

XRPD pattern analysis data of crystalline Form IX of Compound 1

| Nos. | 2θ degree | Relative intensity % | Nos. | 2θ degree | Relative intensity % |
|---|---|---|---|---|---|
| 22 | 23.446 | 32.9 | 45 | 39.502 | 2.6 |
| 23 | 24.055 | 100.0 | | | |

Figure 26:
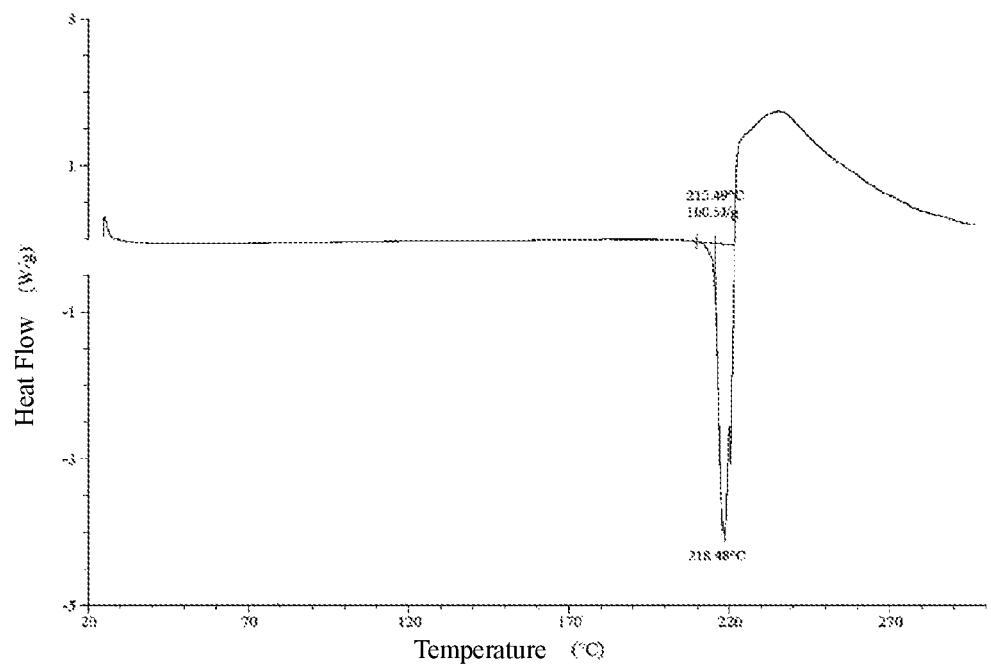

In some embodiments of the present invention, a DSC pattern of said crystalline Form IX of Compound 1 is as shown in FIG. 26.

Figure 27:
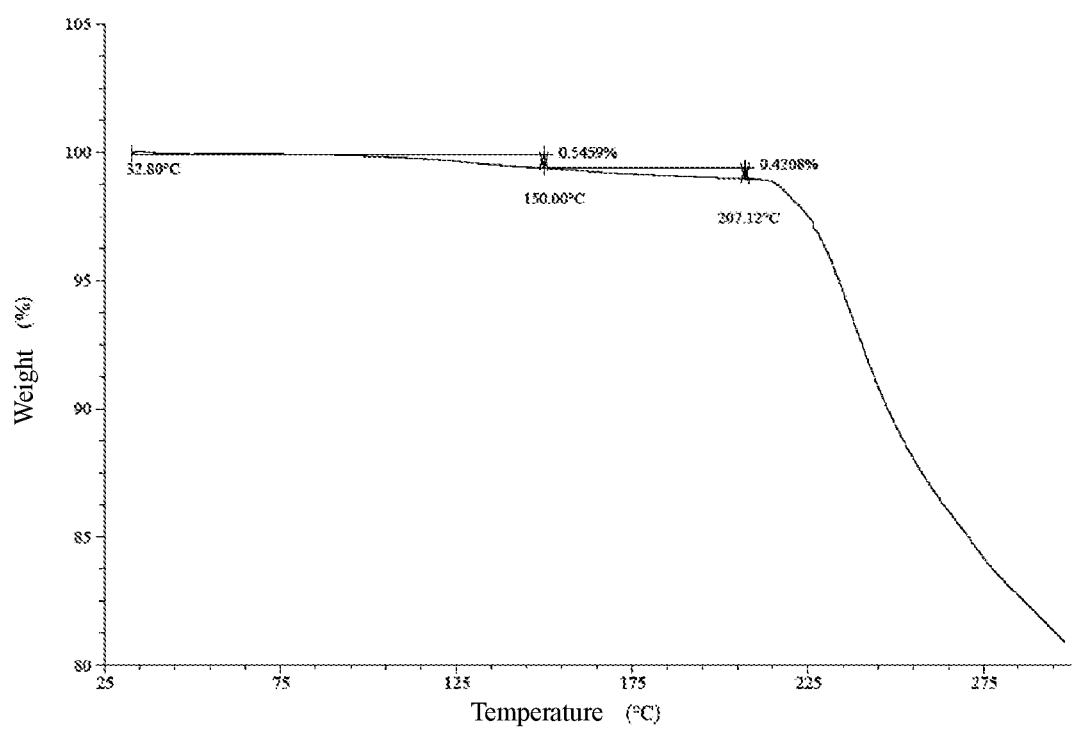

In some embodiments of the present invention, a TGA pattern of said crystalline Form IX of Compound 1 is as shown in FIG. 27.

Crystalline Form IX of Compound 1 can be presented in the form of a non-solvate crystal or a solvate crystal. The solvate herein refers to a solvate that is formed by an organic solvent and/or water with a corresponding compound.

The present invention provides a crystalline composition of crystalline Form IX. In some embodiments of the present invention, crystalline Form IX is present in 50% or more, preferably 80% or more, more preferably 90% or more, most preferably 95% or more of the weight of the crystalline composition.

The present invention provides a pharmaceutical composition of crystalline Form IX, comprising a therapeutically effective amount of crystalline Form IX or a crystalline composition of crystalline Form IX. Furthermore, the pharmaceutical composition may or may not contain pharmaceutically acceptable carriers, excipients and/or media.

The present invention provides Compound 2 represented by the following formula:

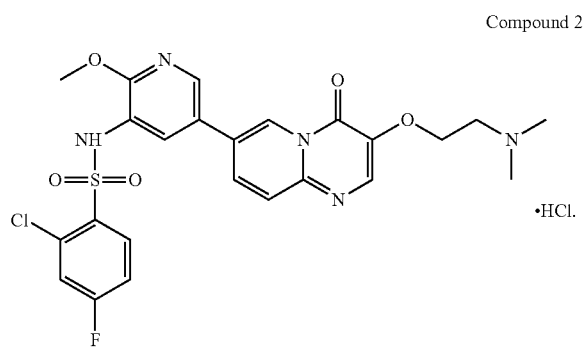 [SMILES: COc1ncc(-c2ccc3ncc(OCCN(C)C)c(=O)n3c2)cc1NS(=O)(=O)c1ccc(F)cc1Cl]

Compound 2

·HCl.

The present invention provides crystalline Form I of Compound 2, characterized by having diffraction peaks at 2θ=10.154°, 12.285°, 14.511°, 16.328°, 24.311°, 26.188°; typically at 2θ=7.270°, 10.154°, 12.285°, 13.206°, 14.511°, 16.328°, 24.311°, 26.188°, 27.724°; more typically at 2θ=7.270°, 10.154°, 12.285°, 13.206°, 14.511°, 16.328°, 19.008°, 20.702°, 21.259°, 24.311°, 26.188°, 27.724°, in a X-ray diffraction (XRD) pattern.

The present invention provides crystalline Form I of Compound 2, which has a XRPD pattern as shown in FIG. 1.

In some embodiments of the present invention, XRPD pattern analysis data of said crystalline Form I of Compound 2 is shown in Table 2.

TABLE 2

XRPD pattern analysis data of crystalline Form I of Compound 2

| Nos. | 2θ degree | Relative intensity % |
|---|---|---|
| 1 | 7.270 | 18.4 |
| 2 | 10.154 | 80.7 |
| 3 | 11.745 | 1.5 |
| 4 | 12.285 | 39.9 |
| 5 | 13.206 | 31.7 |
| 6 | 14.511 | 100.0 |
| 7 | 15.119 | 8.1 |
| 8 | 15.771 | 4.6 |
| 9 | 16.328 | 40.2 |
| 10 | 16.861 | 2.7 |
| 11 | 17.568 | 10.7 |
| 12 | 18.653 | 9.9 |
| 13 | 19.008 | 18.0 |
| 14 | 19.919 | 7.5 |
| 15 | 20.702 | 14.1 |
| 16 | 21.259 | 14.0 |
| 17 | 21.712 | 5.4 |
| 18 | 23.169 | 86.9 |
| 19 | 23.567 | 12.7 |
| 20 | 24.311 | 32.1 |
| 21 | 24.903 | 14.3 |
| 22 | 25.318 | 6.8 |
| 23 | 26.188 | 55.8 |
| 24 | 27.724 | 31.3 |
| 25 | 28.809 | 12.4 |
| 26 | 29.225 | 3.7 |
| 27 | 30.288 | 14.2 |
| 28 | 30.584 | 7.4 |
| 29 | 31.196 | 5.5 |
| 30 | 31.531 | 20.5 |
| 31 | 31.767 | 20.5 |
| 32 | 32.735 | 23.6 |
| 33 | 33.860 | 1.8 |
| 34 | 35.356 | 9.4 |
| 35 | 36.585 | 1.4 |
| 36 | 38.236 | 6.7 |

Figure 2:
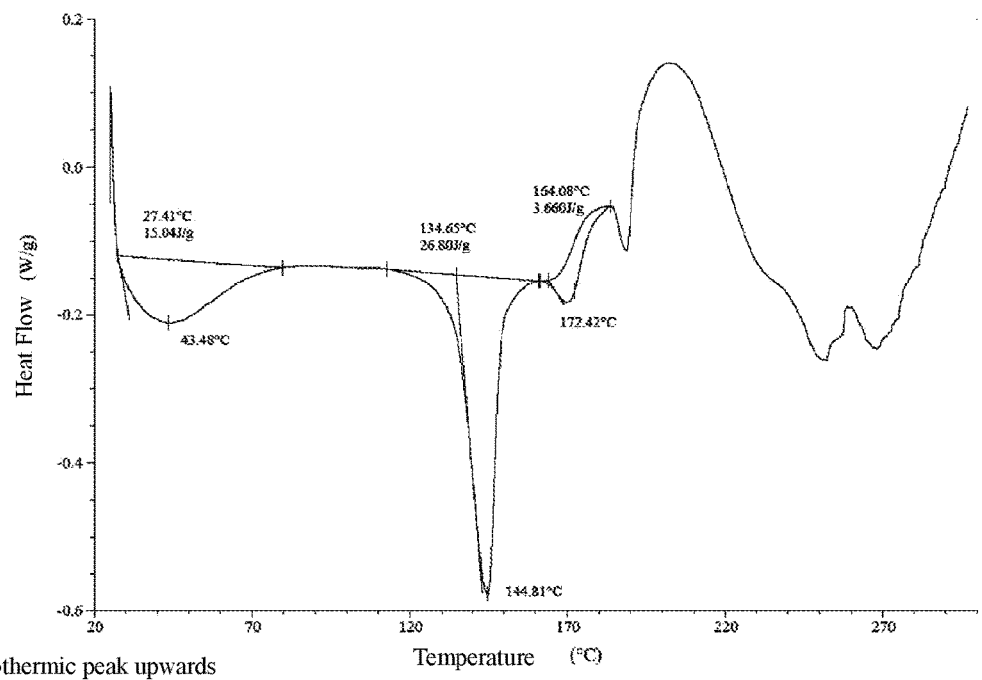

In some embodiments of the present invention, a DSC pattern of crystalline Form I of Compound 2 is as shown in FIG. 2.

Figure 3:
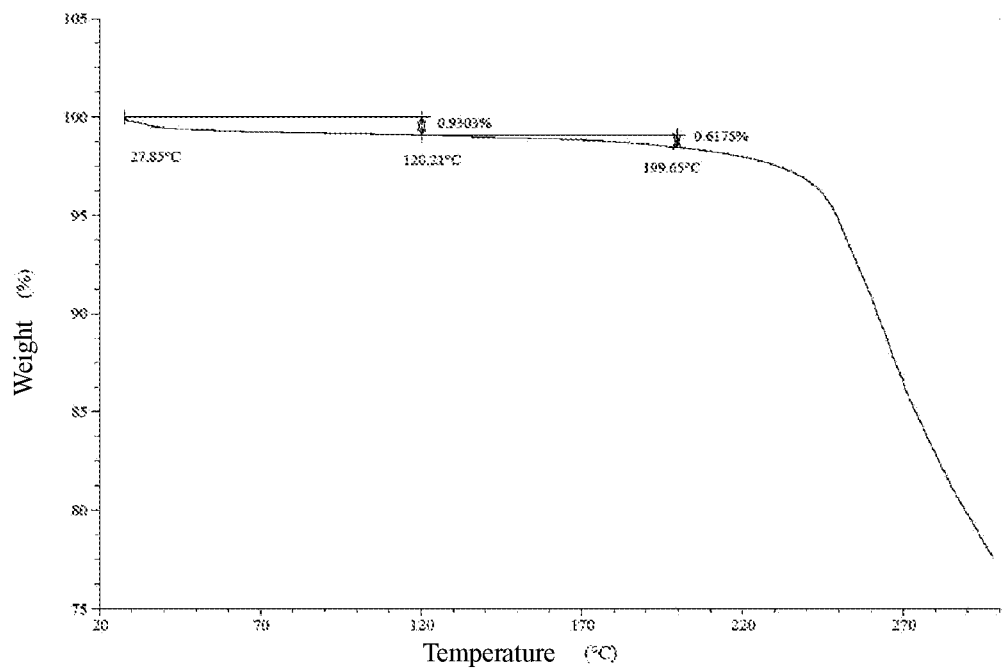

In some embodiments of the present invention, a TGA pattern of crystalline Form I of Compound 2 is shown in FIG. 3.

Crystalline Form I of Compound 2 can be presented in the form of a non-solvate crystal or a solvate crystal. The solvate herein refers to a solvate that is formed by an organic solvent and/or water with a corresponding compound.

The present invention provides a crystalline composition of crystalline Form I. In some embodiments of the present invention, crystalline Form I is present in 50% or more, preferably 80% or more, more preferably 90% or more, most preferably 95% or more of the weight of the crystalline composition.

The present invention provides a pharmaceutical composition of crystalline Form I, comprising a therapeutically effective amount of crystalline Form I or a crystalline composition of crystalline Form I. Furthermore, the pharmaceutical composition may or may not contain pharmaceutically acceptable carriers, excipients and/or media.

The present invention provides crystalline Form II of Compound 2, characterized by having diffraction peaks at 2θ=6.524°, 7.782°, 13.895°, 15.495°, 17.487°, 19.322°; typically at 2θ=6.524°, 7.782°, 11.628°, 13.895°, 15.495°, 17.487°, 19.322°, 20.962°, 23.269°; more typically at 2θ=6.524°, 7.782°, 11.628°, 13.895°, 15.495°, 17.487°, 19.322°, 20.962°, 23.269°, 24.257°, 26.009°, 31.533°, in a X-ray diffraction (XRD) pattern.

Figure 4:
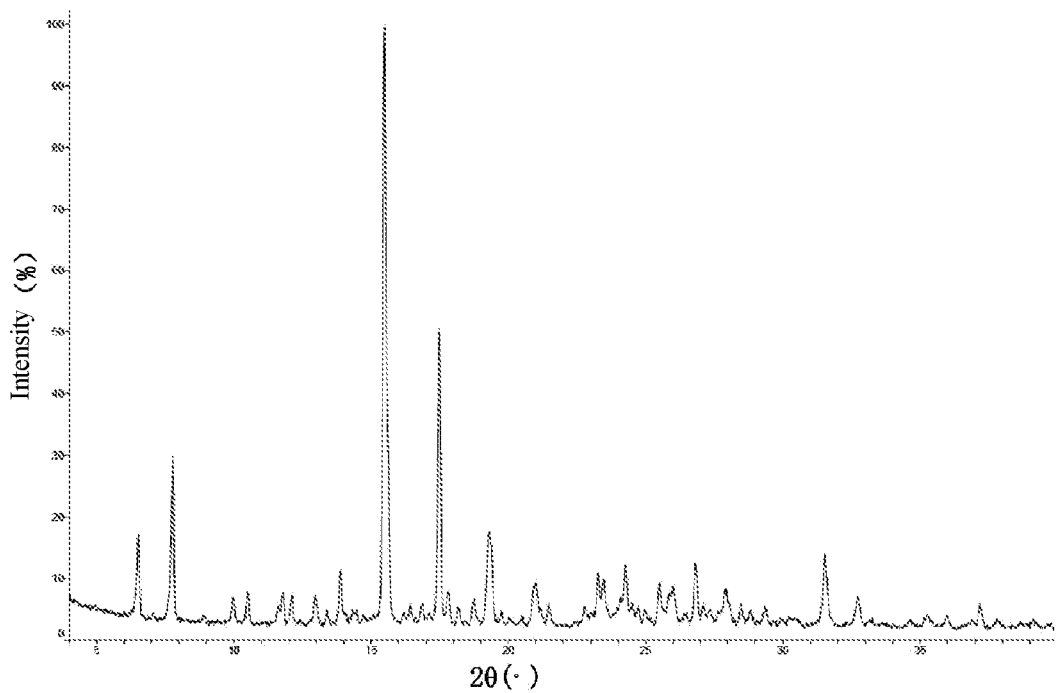

The present invention provides crystalline Form II of Compound 2, which has a XRPD pattern as shown in FIG. 4.

In some embodiments of the present invention, XRPD pattern analysis data of crystalline Form II of Compound 2 is shown in Table 3.

TABLE 3

XRPD pattern analysis data of crystalline Form II of Compound 2

| Nos. | 2θ degree | Relative intensity % |
|---|---|---|
| 1 | 6.524 | 11.3 |
| 2 | 7.782 | 22.3 |
| 3 | 8.879 | 1.0 |
| 4 | 9.977 | 4.7 |
| 5 | 10.494 | 4.4 |
| 6 | 11.628 | 6.7 |
| 7 | 11.804 | 7.5 |
| 8 | 12.122 | 4.5 |
| 9 | 12.973 | 4.7 |
| 10 | 13.406 | 1.1 |
| 11 | 13.895 | 6.7 |
| 12 | 15.495 | 100.0 |
| 13 | 16.423 | 3.0 |
| 14 | 16.860 | 1.9 |
| 15 | 17.131 | 2.0 |
| 16 | 17.487 | 41.7 |
| 17 | 17.807 | 4.7 |
| 18 | 18.181 | 1.8 |
| 19 | 18.749 | 3.3 |
| 20 | 19.322 | 22.3 |
| 21 | 19.740 | 1.9 |
| 22 | 20.962 | 11.4 |
| 23 | 21.474 | 3.5 |
| 24 | 23.269 | 10.9 |
| 25 | 23.481 | 9.6 |
| 26 | 24.257 | 13.8 |
| 27 | 24.515 | 4.9 |
| 28 | 25.515 | 8.0 |
| 29 | 26.009 | 13.9 |
| 30 | 26.818 | 8.4 |
| 31 | 27.095 | 5.1 |
| 32 | 27.350 | 3.3 |
| 33 | 27.648 | 5.5 |
| 34 | 27.922 | 9.0 |
| 35 | 28.477 | 2.5 |
| 36 | 28.810 | 2.9 |
| 37 | 29.343 | 3.4 |
| 38 | 31.533 | 16.1 |
| 39 | 32.733 | 6.0 |
| 40 | 33.263 | 2.9 |
| 41 | 35.260 | 4.9 |
| 42 | 37.173 | 5.8 |

Figure 5:
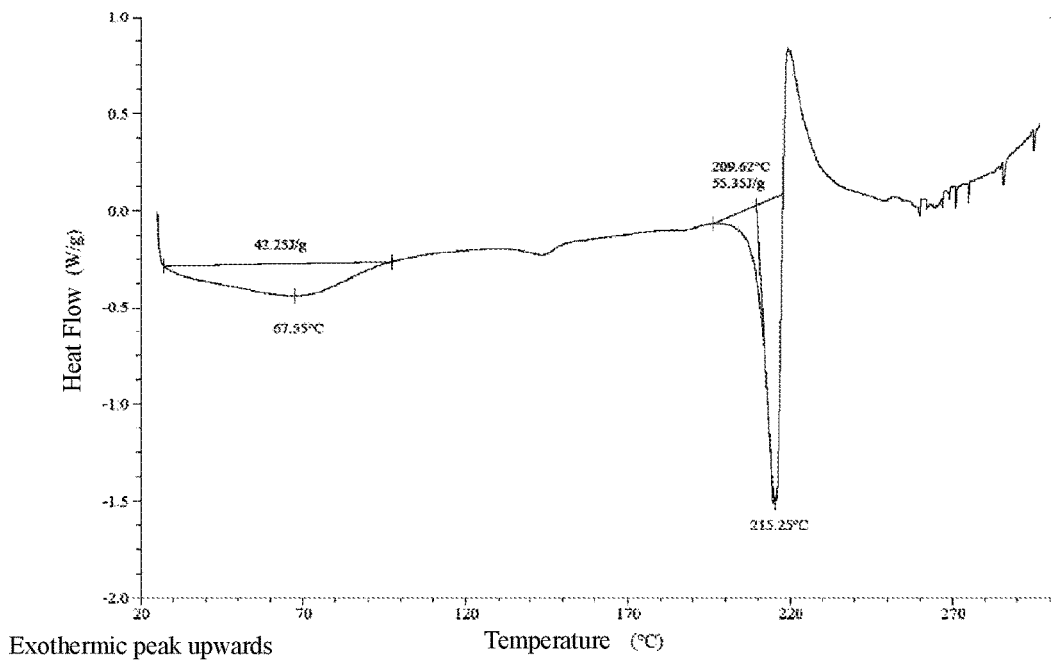

In some embodiments of the present invention, a DSC pattern of crystalline Form II of Compound 2 is as shown in FIG. 5.

Figure 6:
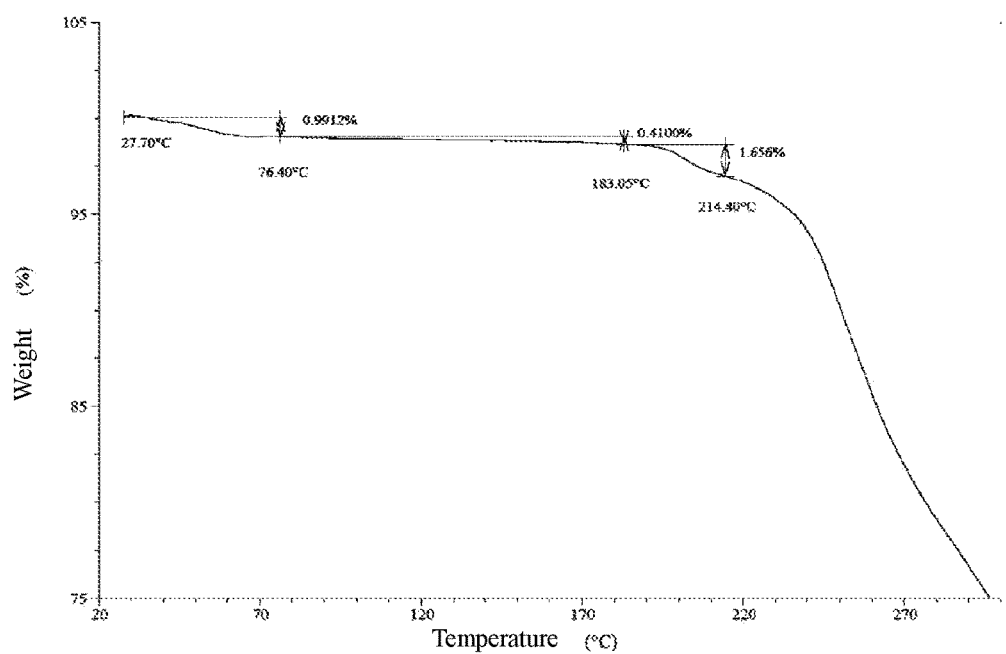

In some embodiments of the present invention, a TGA pattern of crystalline Form II of Compound 2 is as shown in FIG. 6.

Crystalline Form II of Compound 2 can be presented in the form of a non-solvate crystal or a solvate crystal. The solvate herein refers to a solvate that is formed by an organic solvent and/or water with a corresponding compound.

The present invention provides a crystalline composition of crystalline Form II. In some embodiments of the present invention, crystalline Form II is present in 50% or more, preferably 80% or more, more preferably 90% or more, most preferably 95% or more of the weight of the crystalline composition.

The present invention provides a pharmaceutical composition of crystalline Form II, comprising a therapeutically effective amount of crystalline Form II or a crystalline composition of crystalline Form II. Furthermore, the pharmaceutical composition may or may not contain pharmaceutically acceptable carriers, excipients and/or media.

The present invention provides crystalline Form III of Compound 2, characterized by having diffraction peaks at 2θ=6.979°, 9.939°, 14.392°, 16.107°, 20.982°, 25.990°; typically at 2θ=6.187°, 6.979°, 9.939°, 11.910°, 14.392°, 16.107°, 20.982°, 22.755°, 25.990°; more typically at 2θ=6.187°, 6.979°, 9.939°, 11.910°, 13.148°, 14.392°, 16.107°, 20.982°, 22.755°, 23.975°, 25.990°, 29.006°, in a X-ray diffraction (XRD) pattern.

Figure 7:
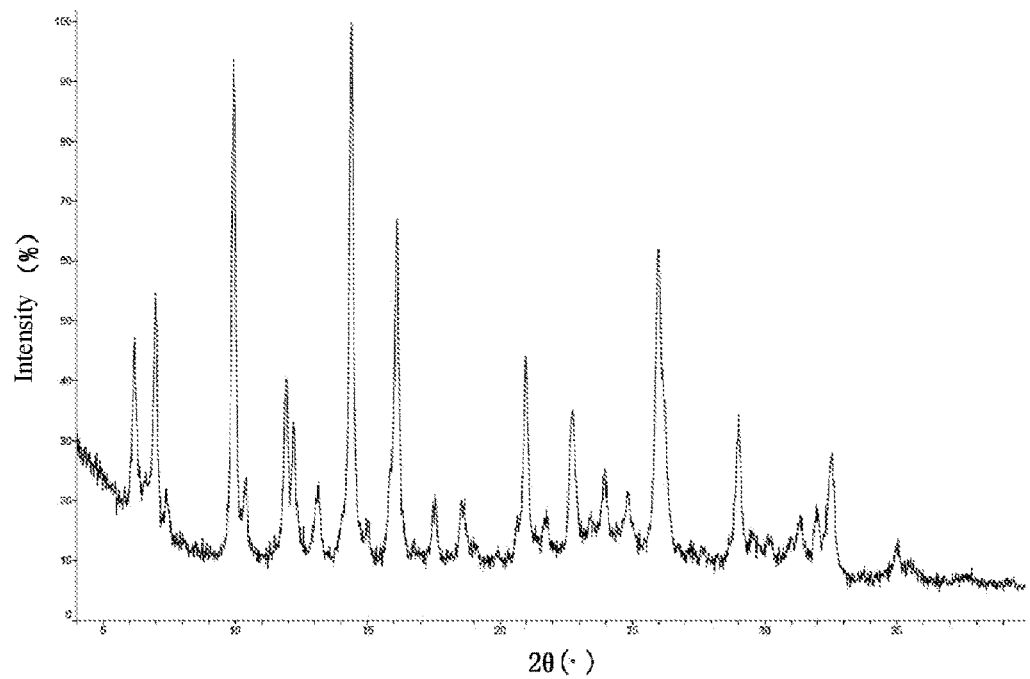

The present invention provides crystalline Form III of Compound 2, which has a XRPD pattern as shown in FIG. 7.

In some embodiments of the present invention, XRPD pattern analysis data of said crystalline Form III of Compound 2 is shown in Table 4.

TABLE 4

XRPD pattern analysis data of crystalline Form III of Compound 2

| Nos. | 2θ degree | Relative intensity % |
|---|---|---|
| 1 | 6.187 | 29.0 |
| 2 | 6.979 | 46.3 |
| 3 | 9.939 | 80.4 |
| 4 | 10.425 | 19.8 |
| 5 | 11.910 | 38.0 |
| 6 | 12.206 | 29.4 |
| 7 | 13.148 | 12.2 |
| 8 | 14.392 | 100.0 |
| 9 | 16.107 | 66.4 |
| 10 | 17.531 | 9.5 |
| 11 | 18.648 | 16.3 |
| 12 | 20.665 | 3.7 |
| 13 | 20.982 | 37.9 |
| 14 | 21.772 | 4.4 |
| 15 | 22.755 | 25.0 |
| 16 | 23.436 | 6.8 |
| 17 | 23.975 | 10.9 |
| 18 | 24.811 | 8.7 |
| 19 | 25.990 | 86.1 |
| 20 | 27.224 | 2.9 |
| 21 | 29.006 | 25.6 |
| 22 | 29.522 | 15.5 |
| 23 | 30.979 | 5.3 |
| 24 | 31.373 | 8.5 |
| 25 | 31.966 | 9.7 |
| 26 | 32.556 | 29.3 |
| 27 | 35.061 | 11.2 |
| 28 | 35.527 | 5.6 |

Figure 8:
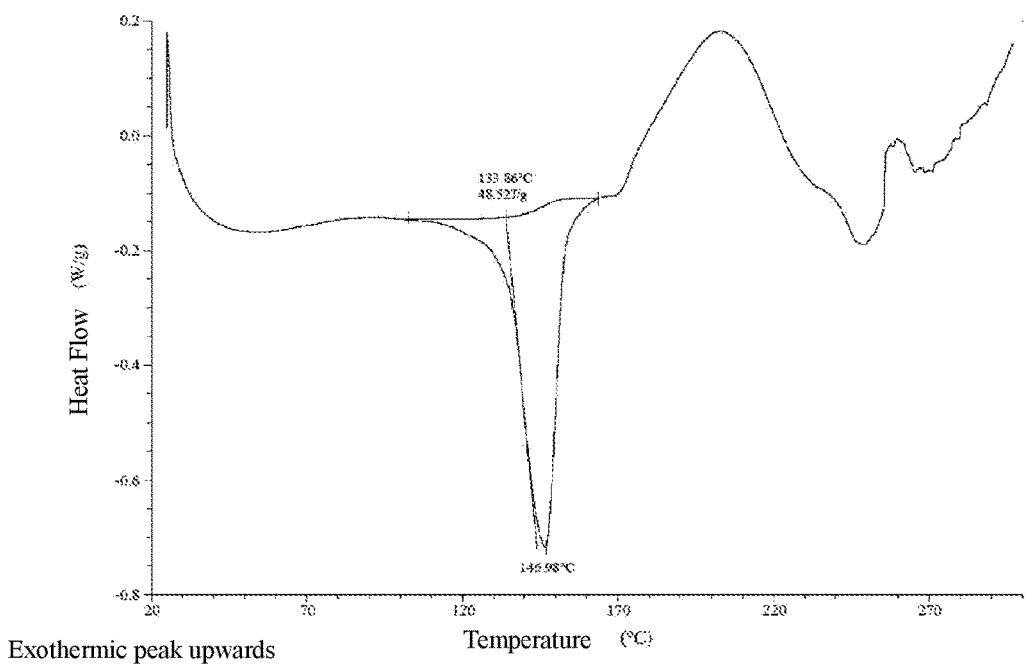

In some embodiments of the present invention, a DSC pattern of crystalline Form III of Compound 2 is as shown in FIG. 8.

Figure 9:
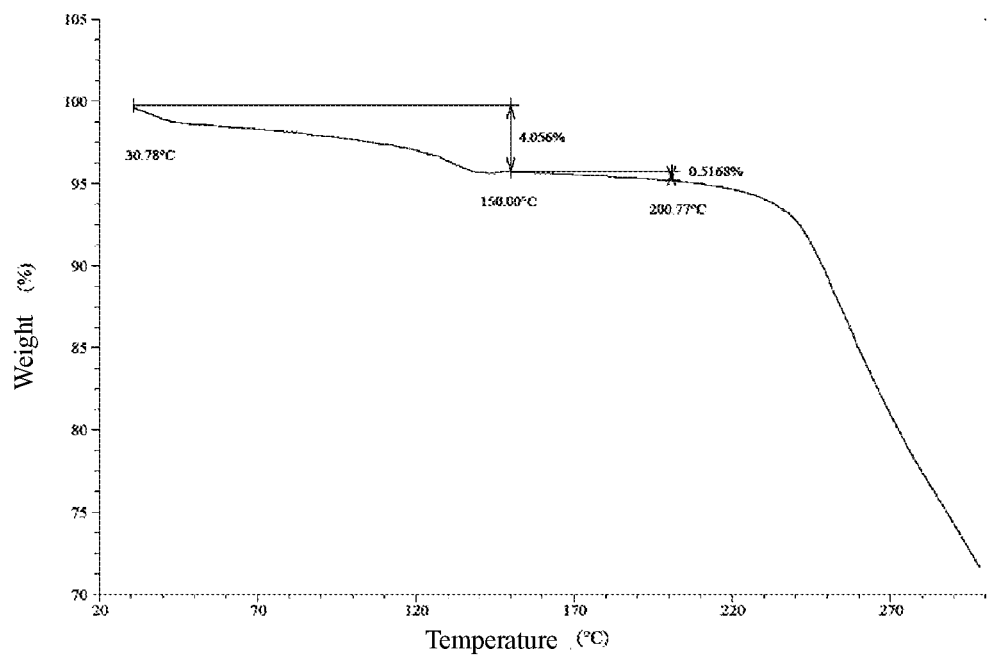

In some embodiments of the present invention, a TGA pattern of crystalline Form III of Compound 2 is as shown in FIG. 9.

Crystalline Form III of Compound 2 can be presented in the form of a non-solvate crystal or a solvate crystal. The solvate herein refers to a solvate that is formed by an organic solvent and/or water with a corresponding compound.

The present invention provides a crystalline composition of crystalline Form III. In some embodiments of the present invention, crystalline Form III is present in 50% or more, preferably 80% or more, more preferably 90% or more, most preferably 95% or more of the weight of the crystalline composition.

The present invention provides a pharmaceutical composition of crystalline Form III, comprising a therapeutically effective amount of crystalline Form III or a crystalline composition of crystalline Form III. Furthermore, the pharmaceutical composition may or may not contain pharmaceutically acceptable carriers, excipients and/or media.

The present invention provides crystalline Form IV of Compound 2, characterized by having diffraction peaks at 2θ=6.388°, 7.278°, 11.076°, 15.454°, 21.256°; typically at 2θ=6.388°, 7.278°, 11.076°, 12.102°, 15.454°, 16.091°, 18.912°, 21.256°; more typically at 2θ=6.388°, 7.278°, 11.076°, 12.102°, 15.103°, 15.454°, 16.091°, 18.912°, 21.256°, 21.846°, in a X-ray diffraction (XRD) pattern.

Figure 10:
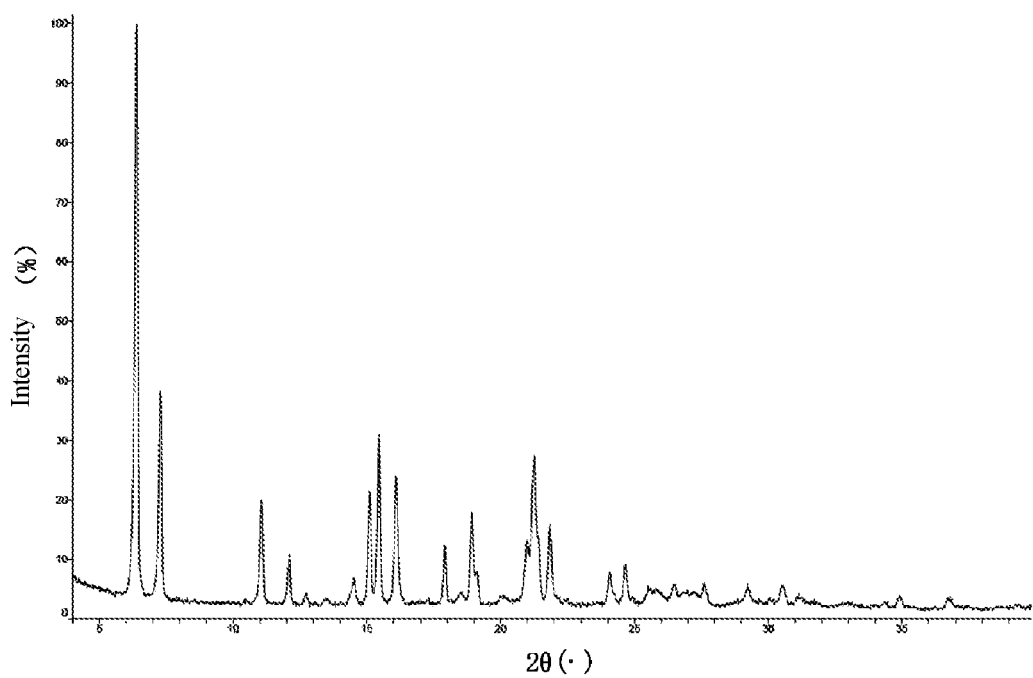

The present invention provides crystalline Form IV of Compound 2, which has a XRPD pattern as shown in FIG. 10.

In some embodiments of the present invention, XRPD pattern analysis data of said crystalline Form IV of Compound 2 is shown in Table 5.

TABLE 5

XRPD pattern analysis data of crystalline Form IV of Compound 2

| Nos. | 2θ degree | Relative intensity % |
|---|---|---|
| 1 | 6.388 | 100.0 |
| 2 | 7.278 | 34.3 |
| 3 | 10.498 | 0.3 |
| 4 | 11.076 | 20.0 |
| 5 | 12.102 | 7.4 |
| 6 | 12.732 | 1.7 |
| 7 | 13.447 | 1.7 |
| 8 | 14.513 | 5.5 |
| 9 | 15.103 | 19.3 |
| 10 | 15.454 | 27.6 |
| 11 | 16.091 | 24.8 |
| 12 | 17.299 | 1.6 |
| 13 | 17.906 | 8.6 |
| 14 | 18.552 | 6.2 |
| 15 | 18.912 | 21.7 |
| 16 | 19.107 | 18.6 |
| 17 | 20.051 | 2.1 |
| 18 | 20.998 | 20.8 |
| 19 | 21.256 | 52.5 |
| 20 | 21.846 | 14.6 |
| 21 | 24.093 | 6.3 |
| 22 | 24.651 | 8.7 |
| 23 | 24.925 | 0.9 |
| 24 | 25.502 | 6.8 |
| 25 | 25.830 | 7.6 |
| 26 | 26.466 | 5.3 |
| 27 | 26.819 | 12.5 |
| 28 | 27.214 | 14.1 |
| 29 | 29.226 | 6.8 |
| 30 | 30.069 | 0.9 |
| 31 | 30.507 | 4.8 |
| 32 | 31.137 | 3.1 |
| 33 | 31.724 | 2.3 |
| 34 | 32.965 | 3.0 |
| 35 | 34.353 | 1.7 |
| 36 | 34.906 | 3.7 |
| 37 | 36.798 | 4.4 |

Figure 11:
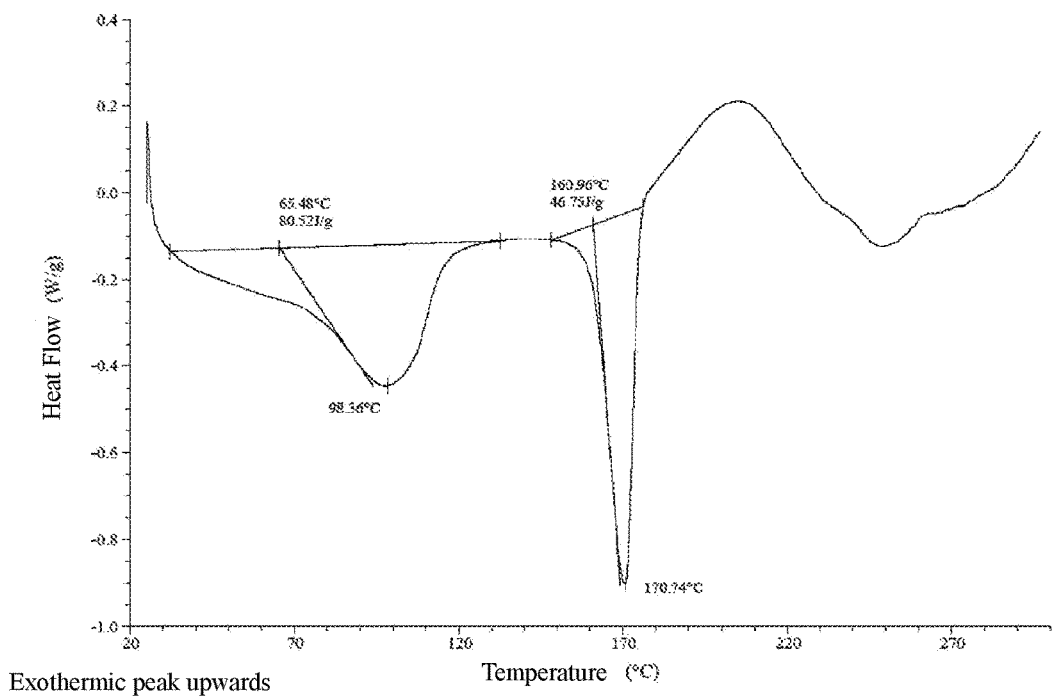

In some embodiments of the present invention, a DSC pattern of crystalline Form IV of Compound 2 is as shown in FIG. 11.

Figure 12:
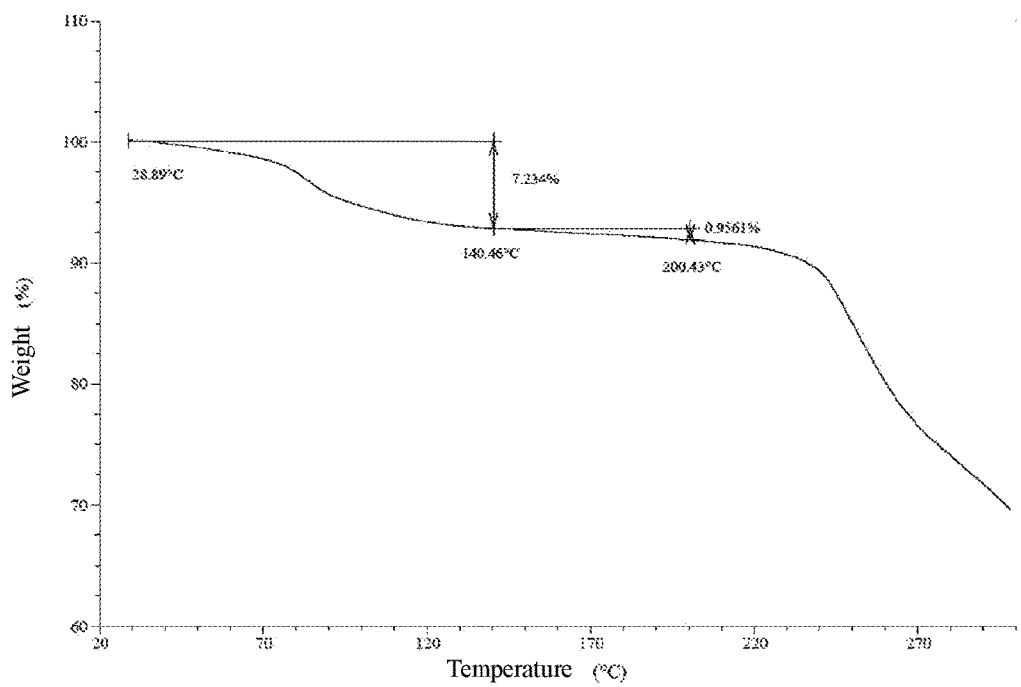

In some embodiments of the present invention, a TGA pattern of crystalline Form IV of Compound 2 is as shown in FIG. 12.

Crystalline Form IV of Compound 2 can be presented in the form of a non-solvate crystal or a solvate crystal. The solvate herein refers to a solvate that is formed by an organic solvent and/or water with a corresponding compound.

The present invention provides a crystalline composition of crystalline Form IV. In some embodiments of the present invention, crystalline Form IV is present in 50% or more, preferably 80% or more, more preferably 90% or more, most preferably 95% or more of the weight of the crystalline composition.

The present invention provides a pharmaceutical composition of crystalline Form IV, comprising a therapeutically effective amount of crystalline Form IV or a crystalline composition of crystalline Form IV. Furthermore, the pharmaceutical composition may or may not contain pharmaceutically acceptable carriers, excipients and/or media.

The present invention provides crystalline Form V of Compound 2, characterized by having diffraction peaks at 2θ=7.116°, 14.137°, 15.911°, 22.223°, 24.610°; typically at 2θ=7.116°, 14.137°, 15.911°, 21.691°, 22.223°, 24.213°, 24.610°, 28.987°, in a X-ray diffraction (XRD) pattern.

Figure 13:
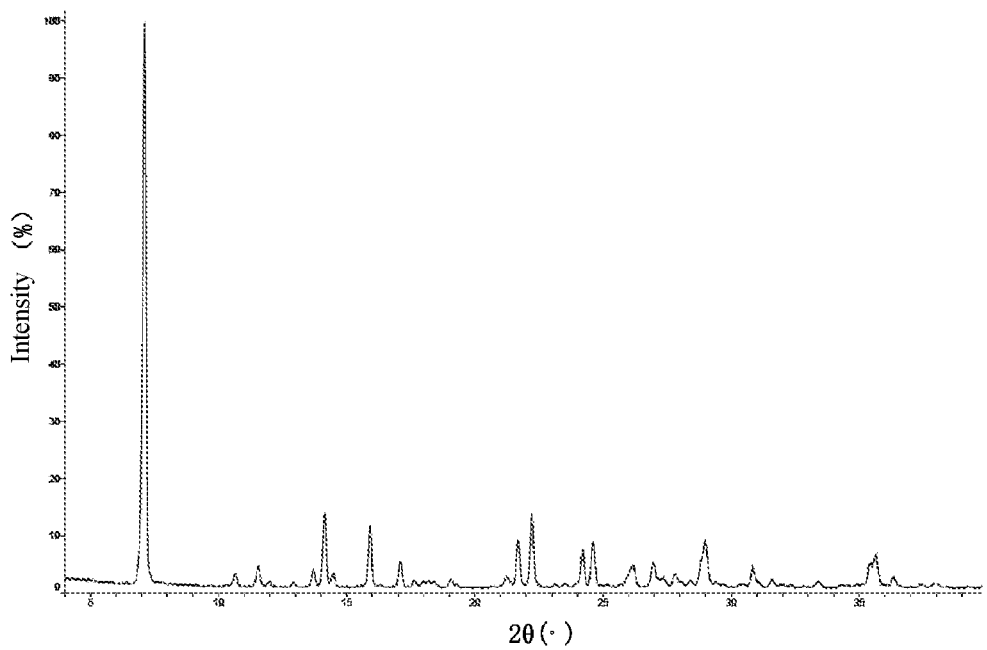

The present invention provides crystalline Form V of Compound 2, which has a XRPD pattern as shown in FIG. 13.

In some embodiments of the present invention, XRPD pattern analysis data of said crystalline Form V of Compound 2 is shown in Table 6.

TABLE 6

XRPD pattern analysis data of crystalline Form V of Compound 2

| Nos. | 2θ degree | Relative intensity % |
|---|---|---|
| 1 | 7.116 | 100.0 |
| 2 | 10.631 | 2.6 |
| 3 | 11.553 | 3.8 |
| 4 | 12.000 | 0.8 |
| 5 | 12.950 | 0.6 |
| 6 | 13.703 | 3.3 |
| 7 | 14.137 | 13.7 |
| 8 | 14.473 | 3.2 |
| 9 | 15.911 | 10.8 |
| 10 | 16.304 | 0.4 |
| 11 | 17.078 | 4.5 |
| 12 | 17.664 | 1.6 |
| 13 | 18.004 | 2.3 |
| 14 | 18.199 | 3.4 |
| 15 | 18.380 | 2.1 |
| 16 | 19.050 | 1.9 |
| 17 | 21.237 | 2.4 |
| 18 | 21.691 | 9.5 |
| 19 | 22.223 | 12.0 |
| 20 | 23.525 | 0.7 |
| 21 | 24.213 | 7.2 |
| 22 | 24.610 | 10.2 |
| 23 | 26.166 | 7.3 |
| 24 | 26.956 | 6.5 |
| 25 | 27.369 | 4.0 |
| 26 | 27.823 | 2.6 |
| 27 | 28.042 | 1.0 |
| 28 | 28.987 | 14.2 |
| 29 | 30.825 | 5.2 |
| 30 | 31.611 | 1.8 |
| 31 | 33.368 | 1.6 |
| 32 | 35.416 | 7.3 |
| 33 | 35.651 | 13.3 |
| 34 | 36.326 | 1.7 |
| 35 | 37.980 | 2.1 |

Figure 14:
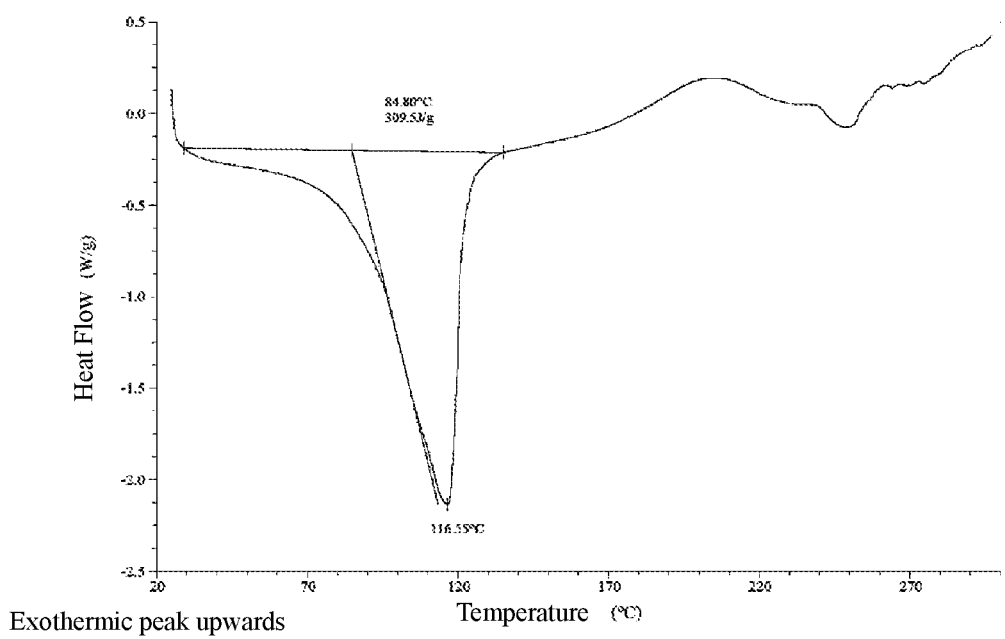

In some embodiments of the present invention, a DSC pattern of crystalline Form V of Compound 2 is as shown in FIG. 14.

Figure 15:
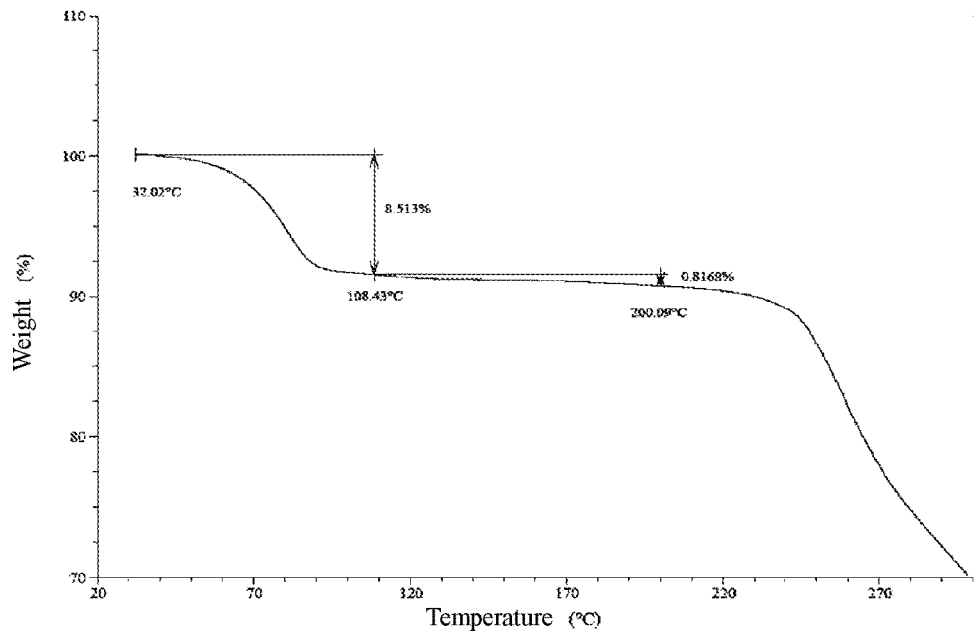

In some embodiments of the present invention, a TGA pattern of crystalline Form V of Compound 2 is as shown in FIG. 15.

Crystalline Form V of Compound 2 can be presented in the form of a non-solvate crystal or a solvate crystal. The solvate herein refers to a solvate that is formed by an organic solvent and/or water with a corresponding compound.

The present invention provides a crystalline composition of crystalline Form V. In some embodiments of the present invention, crystalline Form V is present in 50% or more, preferably 80% or more, more preferably 90% or more, most preferably 95% or more of the weight of the crystalline composition.

The present invention provides a pharmaceutical composition of crystalline Form V, comprising a therapeutically effective amount of crystalline Form V or a crystalline composition of crystalline Form V. Furthermore, the pharmaceutical composition may or may not contain pharmaceutically acceptable carriers, excipients and/or media.

The present invention provides crystalline Form VI of Compound 2, characterized by having diffraction peaks at 2θ=5.775°, 11.770°, 14.415°, 15.753°, 22.518°, 26.623°; typically at 2θ=5.775°, 11.770°, 14.415°, 15.753°, 17.132°, 20.939°, 22.518°, 26.623°; more typically at 2θ=5.775°, 11.770°, 14.415°, 15.753°, 17.132°, 20.939°, 22.518°, 23.745°, 26.623°, 31.295°, in a X-ray diffraction (XRD) pattern.

Figure 16:
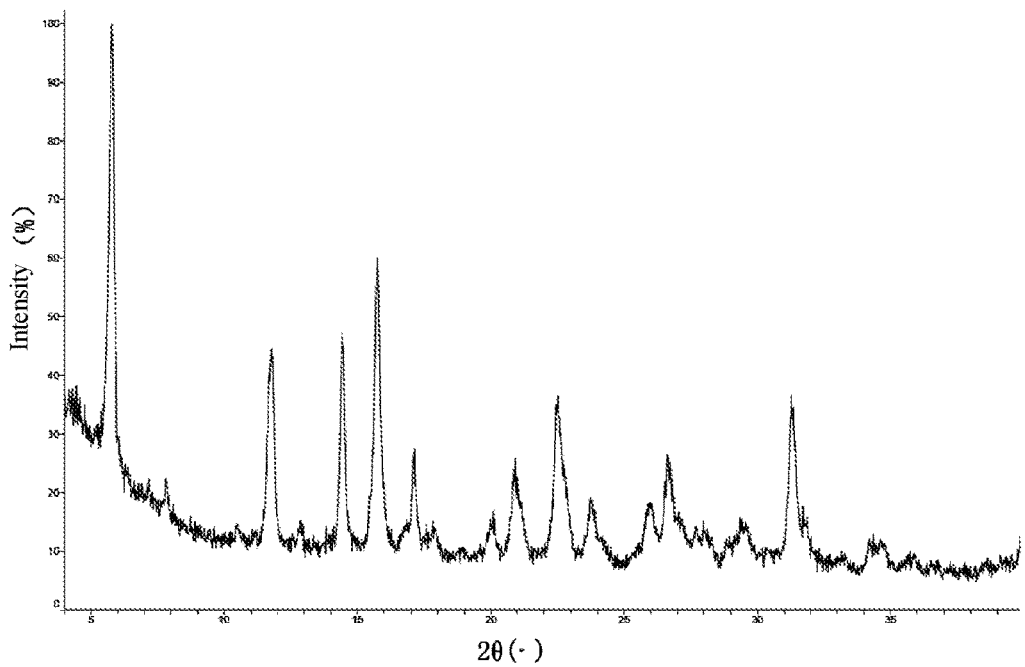

The present invention provides crystalline Form VI of Compound 2, which has a XRPD pattern as shown in FIG. 16.

In some embodiments of the present invention, XRPD pattern analysis data of said crystalline Form VI of Compound 2 is shown in Table 7.

TABLE 7

XRPD pattern analysis data of crystalline Form VI of Compound 2

| Nos. | 2θ degree | Relative intensity % |
|---|---|---|
| 1 | 5.775 | 100.0 |
| 2 | 7.795 | 5.6 |
| 3 | 11.770 | 58.9 |
| 4 | 12.869 | 3.8 |
| 5 | 13.841 | 2.5 |
| 6 | 14.415 | 43.6 |
| 7 | 15.753 | 79.9 |
| 8 | 16.724 | 9.3 |
| 9 | 17.132 | 29.7 |
| 10 | 17.825 | 5.1 |
| 11 | 20.070 | 10.3 |
| 12 | 20.939 | 31.9 |
| 13 | 22.518 | 63.9 |
| 14 | 23.745 | 24.4 |
| 15 | 25.969 | 14.2 |
| 16 | 26.623 | 40.8 |
| 17 | 27.136 | 9.2 |
| 18 | 27.703 | 9.2 |
| 19 | 28.116 | 9.1 |
| 20 | 29.538 | 20.2 |
| 21 | 31.295 | 61.4 |
| 22 | 31.882 | 18.2 |
| 23 | 34.211 | 19.1 |
| 24 | 34.705 | 18.9 |

Figure 17:
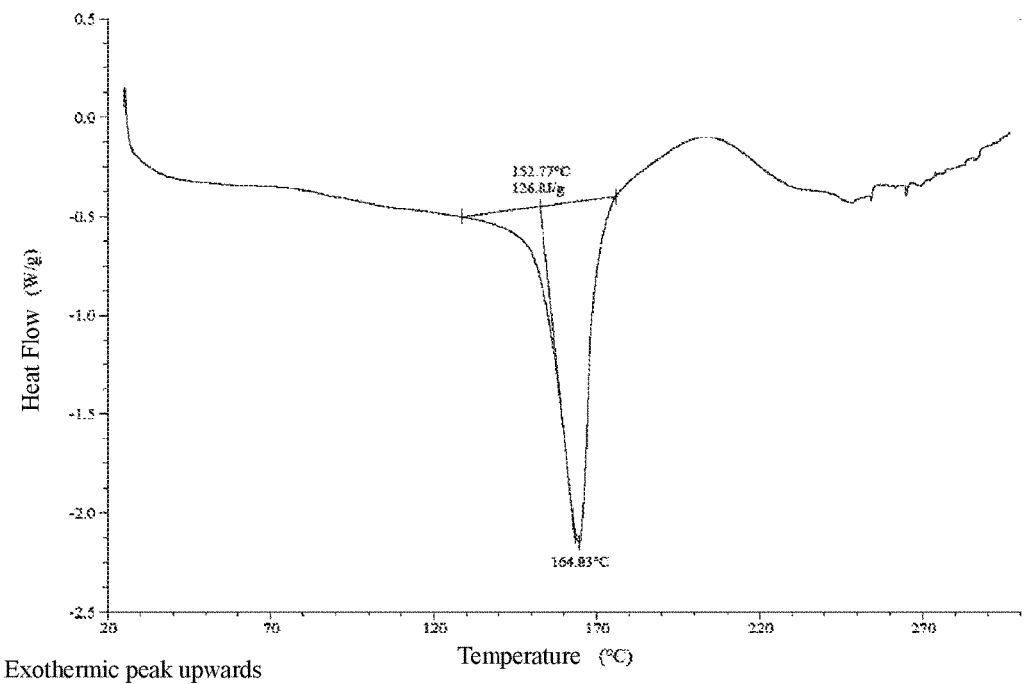

In some embodiments of the present invention, a DSC pattern of crystalline Form VI of Compound 2 is as shown in FIG. 17.

Figure 18:
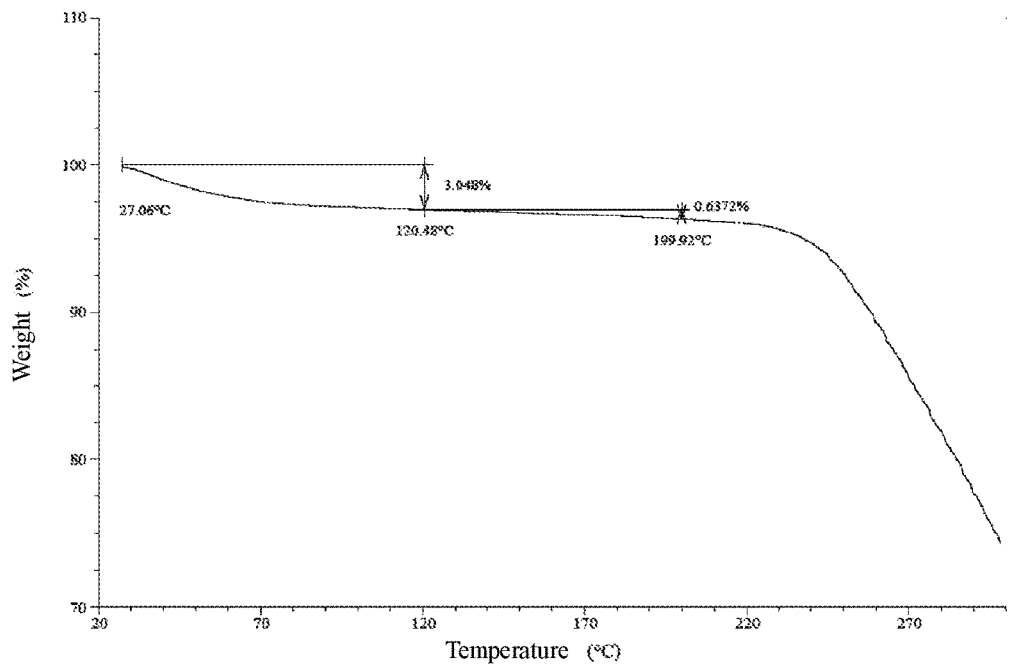

In some embodiments of the present invention, a TGA pattern of crystalline Form VI of Compound 2 is as shown in FIG. 18.

Crystalline Form VI of Compound 2 can be presented in the form of a non-solvate crystal or a solvate crystal. The solvate herein refers to a solvate that is formed by an organic solvent and/or water with a corresponding compound.

The present invention provides a crystalline composition of crystalline Form VI. In some embodiments of the present invention, crystalline Form VI is present in 50% or more, preferably 80% or more, more preferably 90% or more, most preferably 95% or more of the weight of the crystalline composition.

The present invention provides a pharmaceutical composition of crystalline Form VI, comprising a therapeutically effective amount of crystalline Form VI or a crystalline composition of crystalline Form VI. Furthermore, the pharmaceutical composition may or may not contain pharmaceutically acceptable carriers, excipients and/or media.

The present invention provides Compound 3 represented by the following formula:

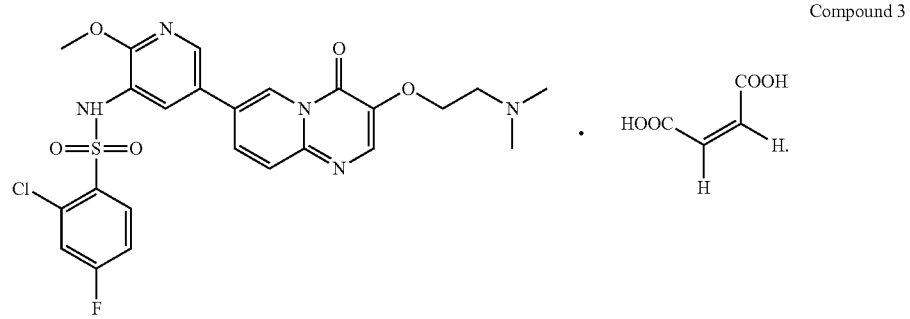

Compound 3

The present invention provides crystalline Form VII of Compound 3, characterized by having diffraction peaks at 2θ=6.325°, 12.677°, 15.813°, 21.395°, 22.519°, 27.133°; typically at 2θ=6.325°, 12.677°, 13.251°, 15.813°, 18.954°, 21.395°, 22.519°, 25.161°, 27.133°; more typically at 2θ=6.325°, 12.677°, 13.251°, 15.813°, 16.565°, 18.954°, 21.395°, 22.519°, 24.117°, 25.161°, 26.405°, 27.133°, in a X-ray diffraction (XRD) pattern.

Figure 19:
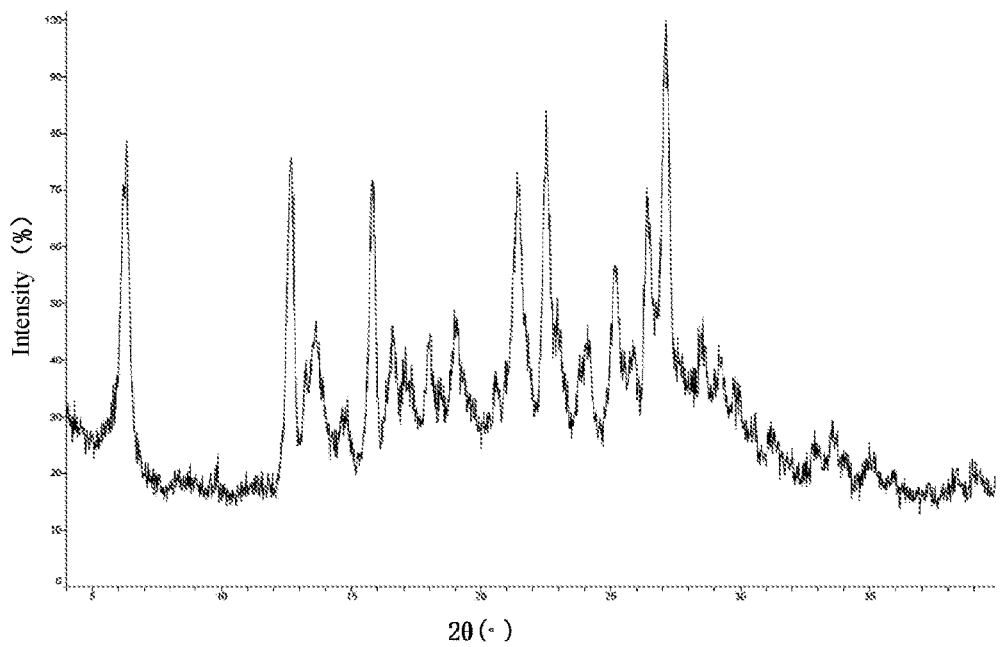

The present invention provides crystalline Form VII of Compound 3, which has a XRPD pattern as shown in FIG. 19.

In some embodiments of the present invention, XRPD pattern analysis data of said crystalline Form VII of Compound 3 is shown in Table 8.

TABLE 8

XRPD pattern analysis data of crystalline Form VII of Compound 3

| Nos. | 2θ degree | Relative intensity % |
|---|---|---|
| 1 | 6.325 | 84.5 |
| 2 | 12.677 | 56.5 |
| 3 | 13.251 | 39.1 |
| 4 | 13.642 | 35.5 |
| 5 | 14.768 | 10.0 |
| 6 | 15.813 | 51.3 |
| 7 | 16.565 | 23.8 |
| 8 | 17.073 | 17.0 |
| 9 | 17.316 | 4.7 |
| 10 | 18.038 | 13.3 |
| 11 | 18.954 | 32.1 |
| 12 | 20.582 | 4.1 |
| 13 | 21.395 | 79.3 |
| 14 | 22.519 | 80.4 |
| 15 | 22.953 | 39.9 |
| 16 | 23.820 | 24.1 |

TABLE 8-continued

XRPD pattern analysis data of crystalline Form VII of Compound 3

| Nos. | 2θ degree | Relative intensity % |
|---|---|---|
| 17 | 24.117 | 24.2 |
| 18 | 25.161 | 47.1 |
| 19 | 25.855 | 11.4 |
| 20 | 26.405 | 41.6 |
| 21 | 27.133 | 100.0 |
| 22 | 28.551 | 17.7 |
| 23 | 29.265 | 16.7 |
| 24 | 31.190 | 7.5 |
| 25 | 32.873 | 7.3 |

TABLE 8-continued

XRPD pattern analysis data of crystalline Form VII of Compound 3

| Nos. | 2θ degree | Relative intensity % |
|---|---|---|
| 26 | 33.581 | 21.2 |
| 27 | 35.155 | 12.1 |

Figure 20:
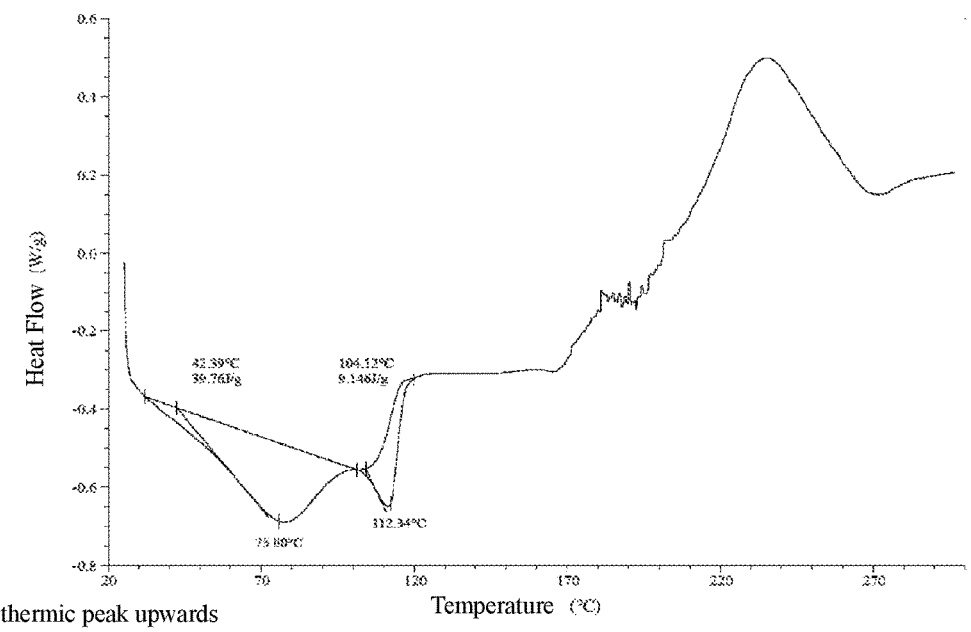

In some embodiments of the present invention, a DSC pattern of crystalline Form VII of Compound 3 is as shown in FIG. 20.

Figure 21:
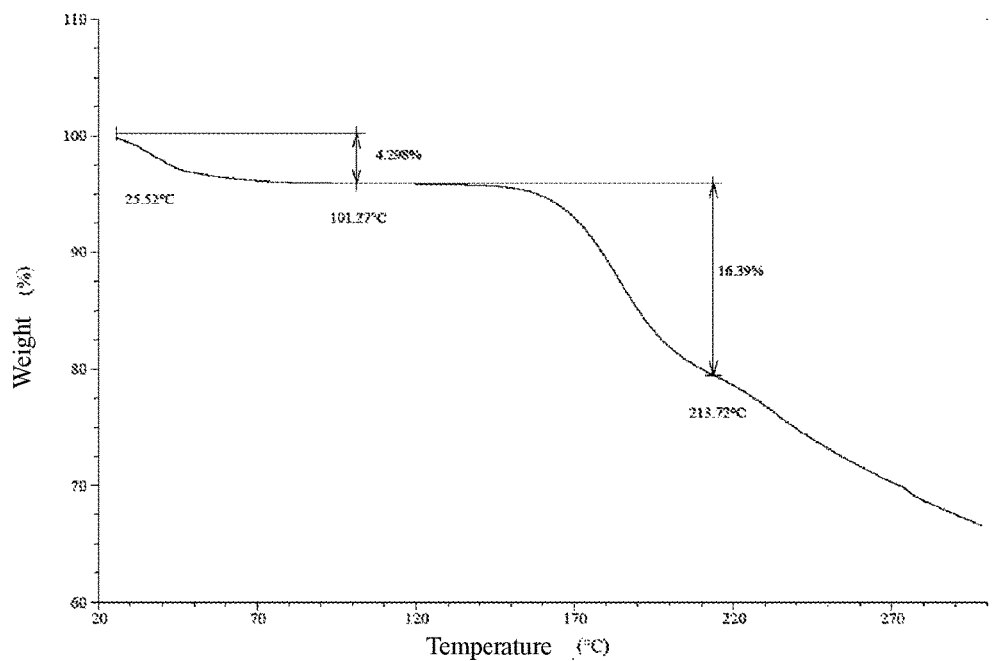

In some embodiments of the present invention, a TGA pattern of crystalline Form VII of Compound 3 is as shown in FIG. 21.

Crystalline Form VII of Compound 3 can be present in the form of a non-solvate crystal or a solvate crystal. The solvate herein refers to a solvate that is formed by an organic solvent and/or water with a corresponding compound.

The present invention provides a crystalline composition of crystalline Form VII. In some embodiments of the present invention, crystalline Form VII is present in 50% or more, preferably 80% or more, more preferably 90% or more, most preferably 95% or more of the weight of the crystalline composition.

The present invention provides a pharmaceutical composition of crystalline Form VII, comprising a therapeutically effective amount of crystalline Form VII or a crystalline composition of crystalline Form VII. Further, the pharmaceutical composition may or may not contain pharmaceutically acceptable carriers, excipients and/or media.

The present invention provides Compound 4 represented by the following formula:

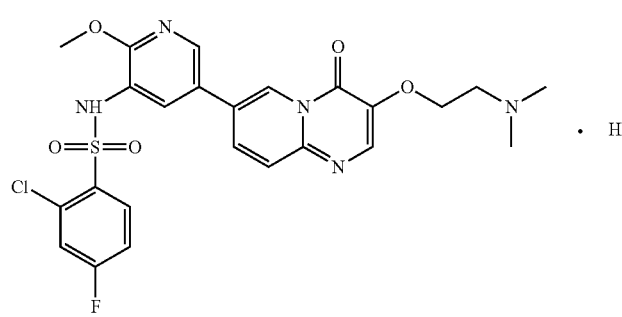
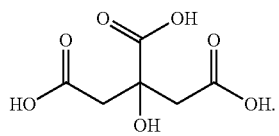

Compound 4

The present invention provides crystalline Form VIII of Compound 4, characterized by having diffraction peaks at 2θ=5.889°, 11.002°, 12.518°, 14.906°, 17.825°, 22.814°, 25.555°; typically at 2θ=5.889°, 7.173°, 11.002°, 11.396°, 12.518°, 12.895°, 14.906°, 17.825°, 22.814°, 25.555°; more typically at 2θ=5.889°, 7.173°, 11.002°, 11.396°, 12.518°, 12.895°, 14.906°, 16.169°, 17.825°, 19.875°, 21.574°, 22.814°, 25.555°, 27.254°, in a X-ray diffraction (XRD) pattern.

Figure 22:
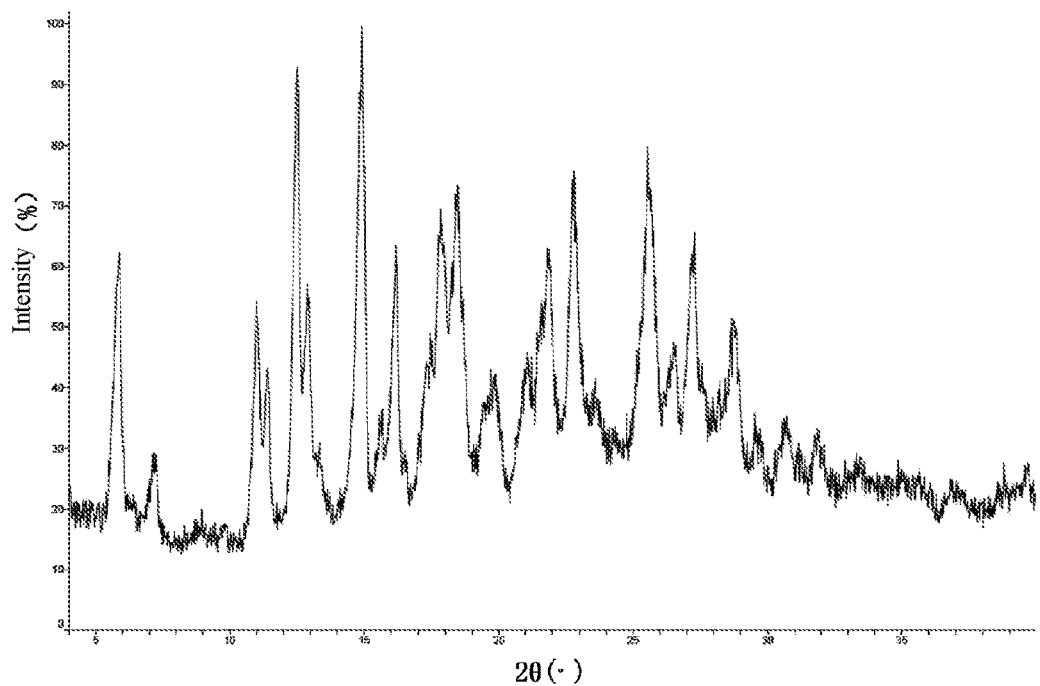

In some embodiments of the present invention, a XRPD pattern of crystalline Form VIII of Compound 4 is as shown in FIG. 22.

In some embodiments of the present invention, XRPD pattern analysis data of said crystalline Form VIII of Compound 4 is shown in Table 9.

TABLE 9

XRPD pattern analysis data of crystalline Form VIII of Compound 4

| Nos. | 2θ degree | Relative intensity % |
| --- | --- | --- |
| 1 | 5.889 | 47.4 |
| 2 | 7.173 | 10.4 |
| 3 | 11.002 | 42.2 |
| 4 | 11.396 | 32.6 |
| 5 | 12.518 | 77.6 |
| 6 | 12.895 | 62.0 |
| 7 | 14.906 | 79.7 |
| 8 | 15.563 | 8.8 |
| 9 | 16.169 | 44.0 |
| 10 | 17.825 | 100.0 |
| 11 | 18.456 | 48.5 |
| 12 | 19.875 | 26.1 |
| 13 | 21.061 | 11.1 |
| 14 | 21.574 | 35.3 |
| 15 | 21.829 | 35.6 |
| 16 | 22.814 | 47.5 |
| 17 | 23.598 | 2.1 |
| 18 | 25.555 | 59.3 |
| 19 | 26.522 | 10.0 |
| 20 | 27.254 | 32.3 |
| 21 | 28.717 | 28.4 |
| 22 | 29.712 | 3.9 |
| 23 | 30.702 | 15.5 |
| 24 | 31.871 | 7.7 |

Figure 23:
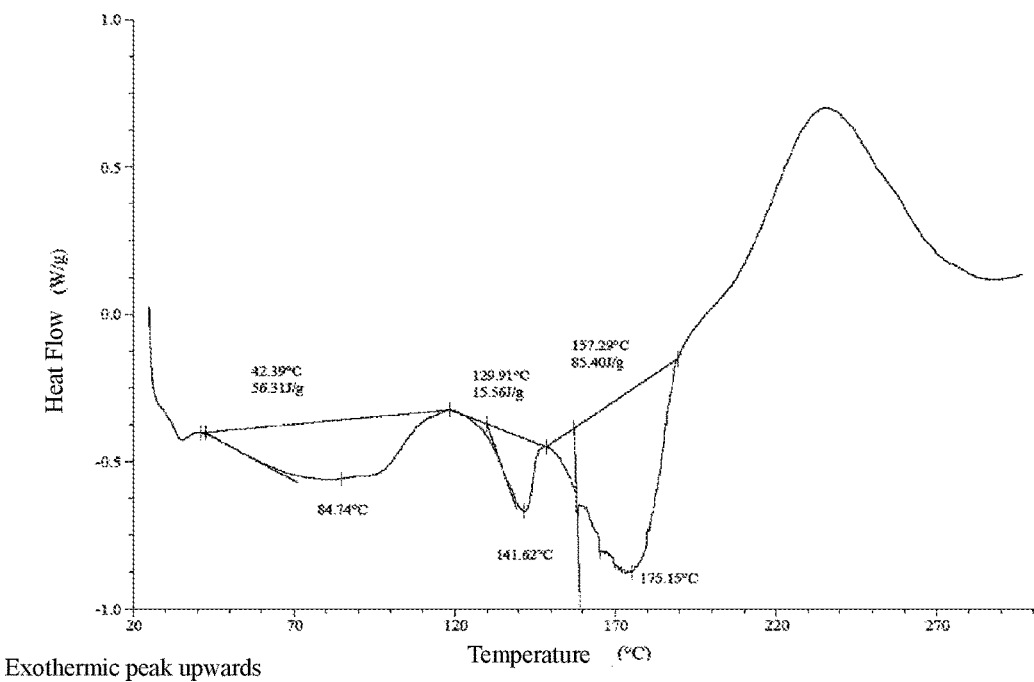

In some embodiments of the present invention, a DSC pattern of crystalline Form VIII of Compound 4 is as shown in FIG. 23.

Figure 24:
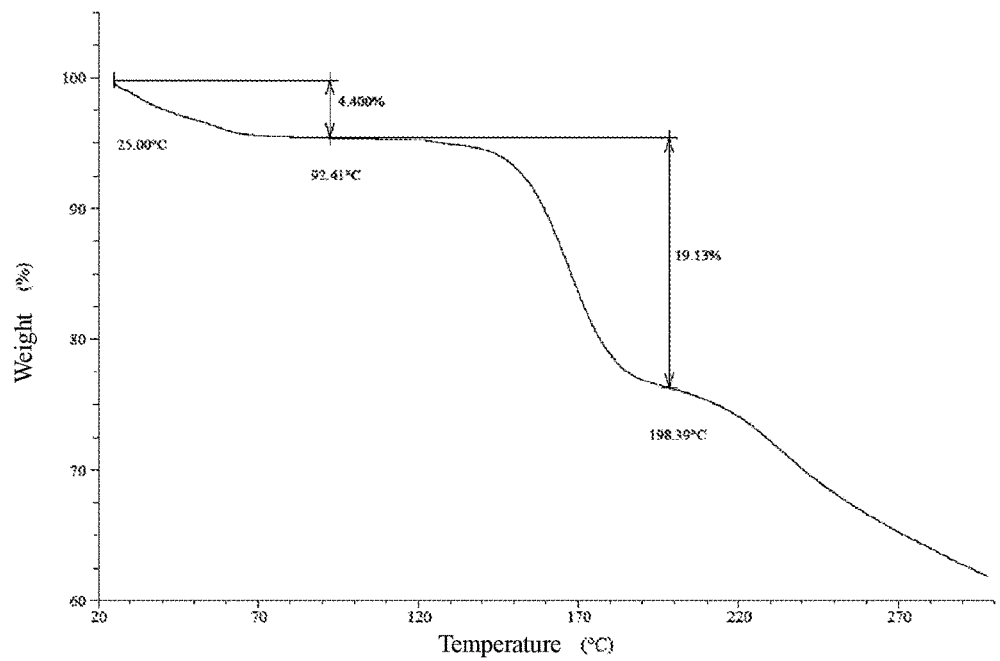

In some embodiments of the present invention, a TGA pattern of crystalline Form VIII of Compound 4 is as shown in FIG. 24.

Crystalline Form VIII of Compound 4 can be presented in the form of a non-solvate crystal or a solvate crystal. The solvate herein refers to a solvate that is formed by an organic solvent and/or water with a corresponding compound.

The present invention provides a crystalline composition of crystalline Form VIII. In some embodiments of the present invention, crystalline Form VIII is present in 50% or more, preferably 80% or more, more preferably 90% or more, most preferably 95% or more of the weight of the crystalline composition.

The present invention provides a pharmaceutical composition of crystalline Form VIII, comprising a therapeutically effective amount of crystalline Form VIII or a crystalline composition of crystalline Form VIII. Furthermore, the pharmaceutical composition may or may not contain pharmaceutically acceptable carriers, excipients and/or media.

An objective of the present invention also is to provide a use of Compounds 1, 2, 3 and 4, or a pharmaceutical composition thereof in the manufacture of a medicament for treating PI3K receptor-related diseases.

Another objective of the present invention is to provide a use of crystalline Forms I, II, III, IV, V, VI, VII, VIII, and IX, a crystalline compositions thereof and a pharmaceutical composition thereof in the manufacture of a medicament for treating PI3K kinase-related diseases.

In some embodiments of the present invention, the PI3K kinase-related diseases are selected from cancer, such as colon cancer, gastric cancer and the like.

An objective of the present invention is to provide a method for treating PI3K kinase-related diseases, comprising administering a therapeutically effective amount of Compounds 1, 2, 3 and 4, or a pharmaceutical composition thereof to a patient in need thereof.

Another objective of the present invention is to provide a method for treating PI3K kinase-related diseases, comprising administering a therapeutically effective amount of crystalline Forms I, II, III, IV, V, VI, VII, VIII and IX of the present invention, a crystalline composition thereof and a pharmaceutical composition thereof to a patient in need thereof.

In some embodiments of the present invention, the PI3K kinase-related diseases are selected from cancer, such as colon cancer, gastric cancer and the like.

Definition and Description

Unless otherwise stated, the terms and phrases used herein are intended to have the following meanings. A specific phrase or term should not be considered uncertain or unclear in the absence of a specific definition, and should be understood according to the common sense. When a trade name appears herein, it is intended to refer to the corresponding product or the active ingredient thereof.

The intermediate compounds of the present invention may be prepared by a variety of synthetic methods well known to the skilled in the art, including the specific embodiments illustrated below, the embodiments formed in conjunction with other chemical synthesis methods, and equivalents well known to the skilled in the art. The preferred embodiments include, but not limited to the examples of the present invention.

The chemical reactions in the specific embodiments of the present invention are accomplished in suitable solvents, which must be suitable for the chemical changes as well as reagents and materials required in the present invention. In order to obtain the compounds of the present invention, it is sometimes necessary for the skilled in the art to modify or select synthesis steps or reaction schemes on the basis of these embodiments herein.

An important consideration factor for any synthetic route planning in the art is selecting a suitable protective group for a reactive functional group (such as the amino group of the present invention). (Protective Groups In Organic Synthesis, Wiley and Sons, 1991) by Greene and Wuts is authority in this field for those trained practitioners in the art. All references cited in the present invention are incorporated herein by reference in its entirety.

The present invention will be specifically described below by examples, but it is not intended that the present invention be limited to these examples.

All solvents used in the present invention are commercially available and used without further purification. The reactions are generally conducted under inert nitrogen gas in the anhydrous solvent. Proton nuclear magnetic resonance data are recorded on a Bruker Avance III 400 (400 MHz) spectrometer, wherein chemical shifts are indicated as (ppm) of tetramethylsilane at low field. Mass spectra are measured on Agilent 1200 Series plus 6110 (&1956A). LC/MS or Shimadzu MS contains a DAD: SPD-M20A (LC) and Shimadzu Micromass 2020 detector. Mass spectrometer is equipped with an electrospray ionization source (ESI) operated under a positive or negative mode.

It should be indicated that in the X-ray diffraction spectrum, the diffraction pattern obtained from a crystalline compound is often characteristic for a specific crystalline Form, in which the relative intensity of the bands (especially at a low angle) may vary due to a dominant orientation effect generated from the difference of crystallization conditions, particle size and other measurement conditions. Therefore, the relative intensity of the diffraction peaks is not characteristic for the targeted crystalline Form. When judging whether a crystalline Form is identical to the known one, what should be noted is the relative positions of peaks rather than the relative intensities thereof. In addition, for any given crystalline Forms, there may be slight error in the positions of the peaks, which is also well known in the field of crystallography. For example, the position of a peak can be moved due to changes in temperature, sample movement, or calibration of instruments during analysis of the sample, and the measurement error of the $2\theta$ value is sometimes about ±0.5°, preferably about ±0.3°, more preferably about ±0.2°. Therefore, when determining the structure of each crystalline Form, such error should be taken into account, and the $2\theta$ values within the error also fall within the scope of the present invention. In a XRD pattern, the position of the peak is usually represented by $2\theta$ angle or interplanar spacing d, and there is a simple conversion formula between them: $d=\lambda/2 \sin \theta$, wherein d represents the interplanar spacing, $\lambda$ represents the wavelength of the incident X-ray, and $\theta$ is the diffraction angle. For the same crystalline Form of the same kind of compound, the positions of the peaks in the XRD spectrums thereof have similarity in the whole, and the relative intensity may have larger error. It should also be pointed out that in the identification of a mixture, parts of the diffraction lines may be lost due to factors such as the decreased content and the like. In this case, even one band may also be characteristic for the given crystal, and it is not necessary to rely on all bands as observed in a high-purity sample.

It should be informed that during preparation of a crystalline Form of a drug, when the drug molecule and a solvent molecule are in contact with each other, it is difficult to avoid that the solvent molecule with the compound molecule form eutectic and remain in the solid due to external conditions and internal factors, thereby forming a solvate, specifically including a stoichiometric and non-stoichiometric solvate. Such solvates are encompassed within the scope of the present invention.

The stoichiometry of chloride ion in Compound 2 (a hydrochloride) prepared by the present invention can be determined by ion chromatography. The instrument used is 883 Basic IC plus 1; the column selected is Metrosep A Supp 5-150/4.0; flow rate of 0.700 mL/min; run time of 10 min.

The present invention employs the following abbreviations: DCM represents dichloromethane; PE represents petroleum ether; EA represents ethyl acetate; DMF represents N,N-dimethylformamide; DMSO represents dimethyl sulfoxide; THF represents tetrahydrofuran; MeOH represents methanol; NMP represents N-methylpyrrolidone; $Et_3N$ represents triethylamine; 4-DMAP represents 4-dimethylaminopyridine; LiOH represents lithium hydroxide; $Cs_2CO_3$ represents cesium carbonate; $K_2CO_3$ represents potassium carbonate; $PPh_3$ represents triphenylphosphine; $Pd(PPh_3)_4$ represents tetra-triphenylphosphine palladium; $Pd(dppf)Cl_2$ represents 1,1'-bis(diphenylphosphino)ferrocene palladium chloride.

X-Ray Powder Diffractometer (XRPD) Method in the Present Invention:
 Instrument Model: Bruker D8 advance X-ray diffractometer
 Test Conditions: detailed XRPD parameters are as follows:
 X-ray generator: Cu, kα, ($\lambda$=1.54056 Å)
 tube voltage: 40 kV, tube current: 40 mA.
 scattering slit: 0.60 mm
 detector slit: 10.50 mm
 anti-scattering slit: 7.10 mm
 scan range: 4-40 deg
 step length: 0.02 deg
 speed: 0.1 S
 rotating speed of a sample plate: 15 rpm Differential Scanning Calorimeter (DSC) Method in the Present Invention:
 Instrument Model: TA Q2000 Differential Scanning Calorimeter
 Test Conditions: a sample (0.5~1 mg) is taken and placed in a DSC aluminum pan for testing, the method is: from room temperature to 300° C., at heating rate of 10° C./min.

Thermal Gravimetric Analyzer (TGA) Method in the Present Invention:
 Instrument Model: TA Q50001R Thermal Gravimetric Analyzer
 Test Conditions: a sample (2~5 mg) is taken and placed in a TGA Platinum pan for testing, the method is: from room temperature to 300° C., at heating rate of 10° C./min.

Technical Effect

Compounds 2, 3, and 4, crystalline Form IX of Compound 1, crystalline Forms I, II, III, IV, V and VI of Compound 2, crystalline Form VII of Compound 3 and crystalline Form VIII of Compound 4 provided in the present invention are stable in nature and have good solubility and excellent hygroscopicity, thus having a promising future to be a drug.

The processes for synthesizing Compound 1 and intermediates thereof provided by the present invention, in which raw materials are cheap and accessible, overcome the disadvantages of high toxicity of reagents used, harsh reaction conditions, difficulties in separation and purification, and not easy to industrialize and the like.

DESCRIPTION OF ATTACHED DRAWINGS

FIG. 1 is a XRPD pattern of crystalline Form I of Compound 2 using Cu-Kα radiation.
FIG. 2 is a DSC pattern of crystalline Form I of Compound 2.
FIG. 3 is a TGA pattern of crystalline Form I of Compound 2.
FIG. 4 is a XRPD pattern of crystalline Form II of Compound 2 using Cu-Kα radiation.
FIG. 5 is a DSC pattern of crystalline Form II of Compound 2.
FIG. 6 is a TGA pattern of crystalline Form II of Compound 2.
FIG. 7 is a XRPD pattern of crystalline Form III of Compound 2 using Cu-Kα radiation.
FIG. 8 is a DSC pattern of crystalline Form III of Compound 2.
FIG. 9 is a TGA pattern of crystalline Form III of Compound 2.
FIG. 10 is a XRPD pattern of crystalline Form IV of Compound 2 using Cu-Kα radiation.
FIG. 11 is a DSC pattern of crystalline Form IV of Compound 2.
FIG. 12 is a TGA pattern of crystalline Form IV of Compound 2.
FIG. 13 is a XRPD pattern of crystalline Form V of Compound 2 using Cu-Kα radiation.
FIG. 14 is a DSC pattern of crystalline Form V of Compound 2.
FIG. 15 is a TGA pattern of crystalline Form V of Compound 2.
FIG. 16 is a XRPD pattern of crystalline Form VI of Compound 2 using Cu-Kα radiation.
FIG. 17 is a DSC pattern of crystalline Form VI of Compound 2.
FIG. 18 is a TGA pattern of crystalline Form VI of Compound 2.
FIG. 19 is a XRPD pattern of crystalline Form VII of Compound 3 using Cu-Kα radiation.
FIG. 20 is a DSC pattern of crystalline Form VII of Compound 3.
FIG. 21 is a TGA pattern of crystalline Form VII of Compound 3.
FIG. 22 is a XRPD pattern of crystalline Form VIII of Compound 4 using Cu-Kα radiation.
FIG. 23 is a DSC pattern of crystalline Form VIII of Compound 4.
FIG. 24 is a TGA pattern of crystalline Form VIII of Compound 4.
FIG. 25 is a XRPD pattern of crystalline Form IX of Compound 1 using Cu-Kα radiation.
FIG. 26 is a DSC pattern of crystalline Form IX of Compound 1.
FIG. 27 is a TGA pattern of crystalline Form IX of Compound 1.

DETAILED DESCRIPTION

In order for the content of the present invention to be better understood, it will be further described by combining the following specific examples which do not constitute any limitations to the content of the present invention.

Reference Example 1: Preparation of Compound 5

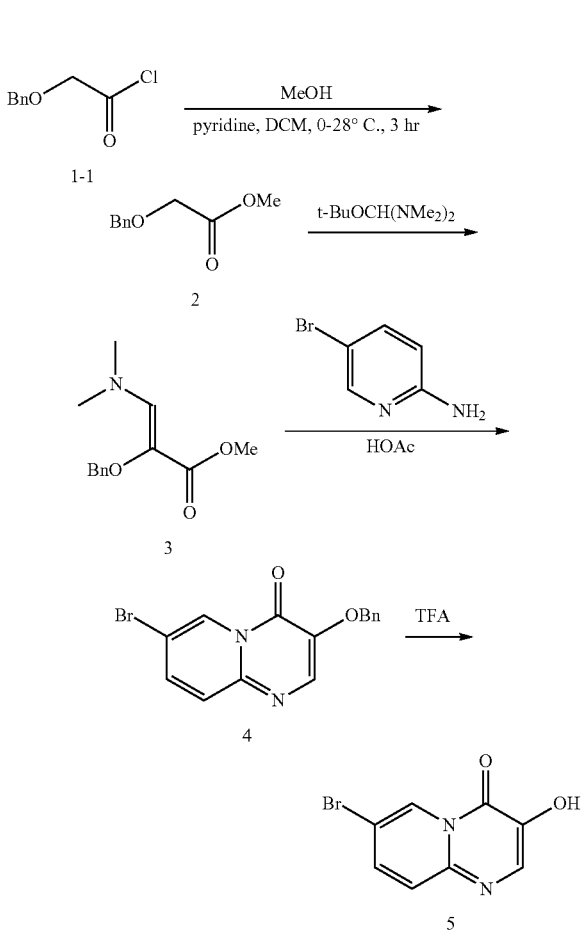

Preparation of methyl 2-(benzyloxy)acetate (2)

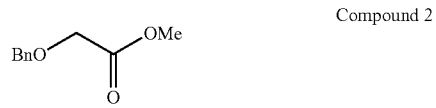 [SMILES: COC(=O)COCc1ccccc1]

Dichloromethane (960 mL) was added in a 3.0 L three-necked round-bottomed flask, methanol (197.6 g, 247 mL) and pyridine (304.78 mL, 311 mol) were added, and the mixture was cooled down to 0° C. in an ice-water bath. Under the protection of nitrogen gas, 2-(benzyloxy)acetyl chloride (300 g, 1.54 mol) was added dropwise into the round-bottomed flask, and the temperature was controlled at 0-10° C. during addition. After the addition, the ice-water bath was removed and the reaction solution was stirred at 20° C. for 1.5 hours. After sampling and detection, TLC (petroleum ether/ethyl acetate=5/1) shows that the reaction was completed. Water (1.5 L) was added to the round-bottomed flask and stirred for 10 minutes, the layers were allowed to separate and the organic layer was collected; the organic layer was then washed with 1.0 mol/L dilute hydrochloric acid (900 mL×2), the layers were allowed to separate and the organic layer was collected; the organic layer was further washed with 20% sodium carbonate solution (600 mL), the layers were allowed to separate, the organic layer was collected, dried with anhydrous sodium sulfate (150 g) and filtered, and the filtrate was concentrated under reduced pressure to give a colorless oil product (284 g, 1.53 mol, 97% yield, 99% purity). $^1$H NMR (400 MHz, chloroform-d) ppm 7.37-7.32 (m, 5H), 4.63 (s, 2H), 4.11 (s, 2H), 3.76 (s, 3H); LCMS (ESI) m/z: 202.8 (M+23).

Preparation of methyl 2-(benzyloxy)-3-(dimethylamino)acrylate (3)

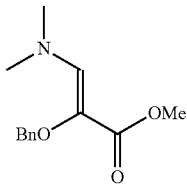

Compound 3

Methyl 2-(benzyloxy)acetate (506 g, 2.72 mol) was added in a 3 L round-bottomed flask, t-butoxybis(dimethylamino)methane (569 g, 3.26 mol) was added, and the reaction temperature was controlled at 90° C.-100° C. to react for 14 hours. After sampling and detection, TLC (PE/EA=5/1) shows that the reaction was completed. The reaction solution was cooled down to 60° C. and concentrated by using an oil pump, to give a yellow oil product (699 g, crude product), which was used directly in the next step.

$^1$H NMR (400 MHz, chloroform-d) ppm 7.44-7.2 (m, 2H), 7.37-7.28 (m, 3H), 6.87 (s, 1H), 4.72 (s, 2H), 3.73 (s, 3H), 2.98 (s, 6H).

Preparation of 3-(benzyloxy)-7-bromo-4H-pyrido[1,2-a]pyrimidin-4-one (4)

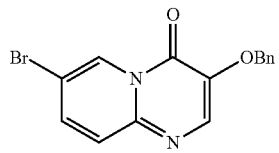

Compound 4

Methyl 2-(benzyloxy)-3-(dimethylamino)acrylate (318 g, 1.35 mol) was added in a 5 L round-bottomed flask, and acetic acid (3 L) and 2-amino-5-bromopyridine (246 g, 1.35 mol) was added thereto. The reaction solution was allowed to react for 14 hours with stirring by controlling the temperature at 120° C.-130° C. After sampling and detection, LCMS shows that the reaction was substantially completed. The reaction solution was cooled down to 60° C., concentrated and evaporated to remove the solvent, added with ethyl acetate (750 mL), stirred for 10 min and filtered. The filter cake obtained was added with ethyl acetate (500 mL), stirred for 10 min and filtered. The further filter cake obtained was rinsed with ethyl acetate (150 mL) and spin-dried to give a yellow solid compound (319 g, 95% purity, 67.79% yield).

$^1$H NMR (400 MHz, chloroform-d) d=9.13 (d, J=2.0 Hz, 1H), 8.05 (s, 1H), 7.56 (dd, J=2.0, 9.6 Hz, 1H), 7.46-7.42 (m, 3H), 7.37-7.33 (m, 3H), 5.30 (s, 2H); LCMS (ESI) m/z: 332.6 (isotope M+1).

Preparation of 7-bromo-3-hydroxy-4H-pyrido[1,2-a]pyrimidin-4-one (5)

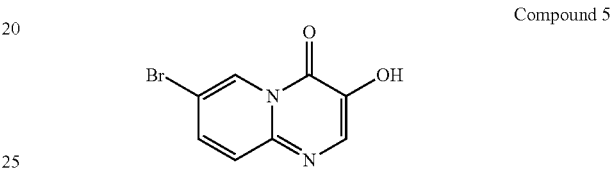

Compound 5

Trifluoroacetic acid (1.2 L) was added in a 3 L round-bottomed flask, 3-(benzyloxy)-7-bromo-4H-pyrido[1,2-a]pyrimidin-4-one (313 g, 897.9 mmol) was added thereto, and the reaction solution was allowed to react for 2 hours with stirring by controlling the temperature at 80° C.-90° C. After sampling and detection, LCMS shows that the reaction was substantially completed. The reaction solution was cooled down to 60° C., concentrated and evaporated to remove the solvent, added with ethyl acetate (1.2 L), stirred for 60 min and filtered. The filter cake obtained was added with ethyl acetate (400 mL), stirred for 60 min and filtered. The further filter cake obtained was dried under reduced pressure at 40° C. for 70 hours, to give a yellow solid compound (191 g, 95.6% content, 100% purity, 84.59% yield).

$^1$H NMR (400 MHz, DMSO-d6) d=9.92 (br, 1H), 8.90 (s, 1H), 8.07 (s, 1H), 7.73 (dd, J=2.0, 9.6 Hz, 1H), 7.53 (d, J=9.6 Hz, 1H); MS m/z: 240.9 (M+1), 242.8 (isotope M+1).

Example 1: Preparation of Compound 1

7-bromo-3-(2-(dimethylamino)ethoxy)-4H-pyrido[1,2-a]pyrimidin-4-one (6)

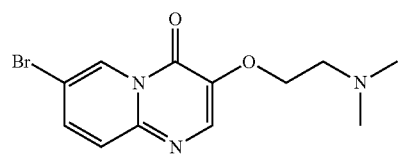

Compound 6

7-bromo-3-hydroxy-4H-pyrido[1,2-a]pyrimidin-4-one (300 g, 1.2 mol) and N,N-dimethylformamide (3 L) were added in a round-bottomed flask and the temperature of the reactor was adjusted to 95° C.-100° C. Potassium carbonate (497.4 g, 3.6 mol) was added in the reaction flask and stirred for 30 min. 2-dimethylaminoethyl chloride hydrochloride was then divided into three portions and fed as follows: adding 2-dimethylaminoethyl chloride hydrochloride (70.6 g, 0.49 mol) in the reaction flask and stirring for 30 min; adding 2-dimethylaminoethyl chloride hydrochloride (70.6 g, 0.49 mol) in the reaction flask and stirring for 30 min; and adding 2-dimethylaminoethyl chloride hydrochloride (70.6 g, 0.49 mol) in the reaction flask and stirring for 2-2.5 hours.

After the reaction was completed (as monitored using HPLC), the temperature of the reactor was adjusted to 15±5° C. The reaction solution was added to water (15 L), followed by extracting with dichloromethane (4.5 L×4). The organic phase was combined and concentrated under reduced pressure at 35±5° C. to constant weight. To the product obtained after concentration, n-heptane (1.8 L) was added and stirred at 15±5° C. for 15-16 hours. After filtration, the filter cake obtained was spin-evaporated under reduced pressure at 35±5° C. to give a green solid product (280 g, 74.09% yield, 98.22% purity).

$^1$H NMR (400 MHz, CDCl$_3$) d=2.35 (s, 6H), 2.78 (t, J=5.6 Hz, 2H), 4.25 (t, J=6.0 Hz, 2H), 7.45 (d, J=9.6 Hz, 1H), 7.55 (dd, J=9.6 Hz, 2 Hz, 1H), 8.13 (s, 1H), 9.09 (d, J=2.0 Hz, 1H); LCMS (ESI) m/z: 312 (isotope M+1).

Preparation of 7-(5-amino-6-methoxypyrimidin-3-yl)-3-(2-(dimethylamino)ethoxy)-pyrido[1,2-a]pyrimidin-4-one (7)

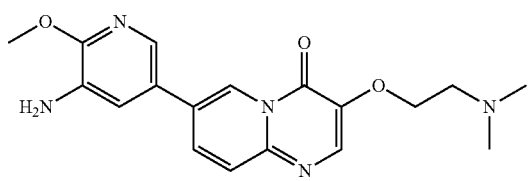

Compound 7

7-bromo-3-(2-(dimethylamino)ethoxy)-4H-pyrido[1,2-a]pyrimidin-4-one (275 g, 0.87 mol), 2-methoxy-5-(4,4,5,5-tetramethyl-1,3,2-dioxaborolan-2-yl)pyridin-3-amine (249 g, 0.96 mol), 1,4-dioxane (2.75 L), water (550 mL) and potassium carbonate (362 g, 2.62 mol) were successively added in a reaction flask; after bubbling for 30-60 min, Pd(dppf)Cl$_2$ (19.2 g, 26 mmol) was added in the reaction flask and the reaction flask was replaced 5 times with nitrogen gas; the temperature of the reaction flask was adjusted to 95±5° C., and the mixture was stirred for 2-2.5 hours at this temperature. After the reaction was completed (as monitored using HPLC), the temperature of the reactor was adjusted to 15±5° C. The reaction solution was added to n-heptane (6.6 L), and after adjusting the temperature to 15±5° C., the mixture was stirred for 2-2.5 hours at this temperature. After filtration, the filter cake obtained was spin-dried under reduced pressure at 45±5° C. The residue obtained was added with dichloromethane/methanol (V/V=8/1, 2.75 L), stirred at 15±5° C. for 30-60 min and filtered to obtain a filter cake; and the filter cake was added with dichloromethane/methanol (V/V=8/1, 1.375 L), stirred for 30-60 min at 15±5° C. and filtered again to obtain another filter cake, which was then rinsed with dichloromethane/methanol (V/V=8/1, 1.375 L). The two filtrates obtained were combined and concentrated under reduced pressure at 45±5° C. The concentrated residue was added with dichloromethane/methanol (V/V=2/1, 4.125 L), and dissolved by stirring. The resulting solution was added with thiocyanuric acid (13.93 g) and activated carbon (27.5 g), stirred at 15±5° C. for 15-16 hours and filtered with diatomaceous earth (137.5 g), and the obtained filter cake was rinsed with dichloromethane/methanol (V/V=2/1, 1.375 L×2). The filtrate was concentrated under reduced pressure at 45±5° C. The concentrated residue was added with methanol (1.1 L), stirred at 15±5° C. for 2-3 hours and filtered, and the obtained filter cake was rinsed with methanol (137.5 mL) and spin-evaporated under reduced pressure at 45±5° C., to give a yellow solid product (270 g, 97.98% purity, 84.24% yield).

$^1$H NMR (400 MHz, DMSO-d6) d=8.92 (d, J=1.6 Hz, 1H), 8.24 (s, 1H), 8.04 (dd, J=9.6 Hz, 2 Hz, 1H), 7.80 (d, J=2 Hz, 1H), 7.67 (d, J=9.6 Hz, 1H), 7.27 (d, J=2.0 Hz, 1H), 5.24 (s, 2H), 4.19 (t, J=6.0 Hz, 2H), 3.93 (s, 3H), 2.66 (t, J=6.0 Hz, 2H), 2.25 (s, 6H); LCMS (ESI) m/z: 356 (M+1).

Preparation of Compound 1

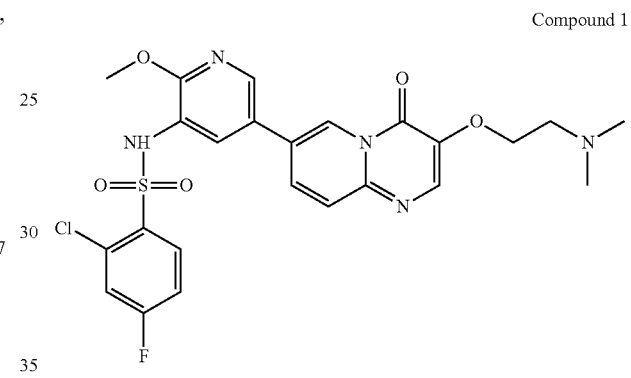

Compound 1

7-(5-amino-6-methoxypyrimidin-3-yl)-3-(2-(dimethylamino)ethoxy)-pyrido[1,2-a]pyrimidin-4-one (265 g, 0.72 mol) and pyridine (2.65 L) were added in a reaction flask; after cooling down to 5±5° C., a solution of 2-chloro-4-fluorobenzenesulfonyl chloride (252 g, 1.08 mol) in pyridine (504 mL) was added dropwise in the reaction flask; when the addition was completed, the reaction solution was adjusted to the temperature of 30° C.-35° C. and stirred for 2-3 hours at this temperature. After the reaction was completed (as monitored using HPLC), the reaction solution was concentrated under reduced pressure at 45±5° C. to a weight that is 2.5-3 times that of Compound 7. The concentrated product was added with dichloromethane (3.7 L), stirred at 25±5° C. for 30 min, and then concentrated under reduced pressure at 45±5° C. to a weight that is 2.5-3 times that of Compound 7. The concentrated product was added with dichloromethane (3.7 L) and slurried at 25±5° C. for 2-3 hours. After filtration, the filter cake was collected and spin-evaporated at 45±5° C. to a weight that is 1.3-1.7 times that of Compound 7. The spin-evaporated product was added with dichloromethane (1.85 L) and slurried at 25±5° C. for 2-3 hours. After filtration, the filter cake was collected, spin-evaporated at 45±5° C. to a weight that is 1.2-1.4 times that of Compound 7 and then vacuum-dried at 45° C. for 3-4 hours to a weight that is 1.2-1.3 times that of Compound 7. The obtained crude product was added with acetonitrile (2.12 L) and slurried at 55±5° C. for 15-16 hours. The solution after slurrying was cooled down to 25±5° C. and filtered, and the obtained filter cake was collected and spin-evaporated at 45±5° C. to a weight that is 1.1-1.2 times that of Compound 7. The spin-evaporated product was added with acetonitrile (1.9 L) and slurried at 55±5° C. for 15-16 hours. The solution after slurrying was cooled down to 25±5° C. and filtered, and the obtained filter cake was spin-evaporated at 45±5° C. to a weight that is 1.0-1.1 times that of Compound 7. The spin-evaporated product was added with methanol (5.3 L) and activated carbon (53 g), and stirred at 75±5° C. for 2-3 hours. The filtration was performed with diatomaceous earth (132 g), and the obtained filter cake was collected, added with a mixed solvent of dichloromethane and methanol (V/V=4/1, 7.95 L) and stirred at 25±5° C. for 30-60 min. The filtration was performed again, and the two filtrates obtained were combined and concentrated at 45±5° C. to a weight that is 1.01-1.03 times that of Compound 7. The concentrated product was added with water (4.24 L) and ethanol (1.06 L), stirred at 25±5° C. for 5-10 min, added dropwise with a saturated sodium hydrogencarbonate aqueous solution (1.3 L) and additionally stirred for 2-3 hours. After filtration, the filter cake was spin-evaporated at 45±5° C. to a weight that is 1.1-1.3 times that of Compound 7. The spin-evaporated product was added with ethanol (1.59 L) and slurried at 75±5° C. for 15-16 hours. The solution after slurrying was cooled down to 25±5° C. and filtered, and the filter cake was collected and spin-evaporated at 45±5° C. to a weight that is 0.89-0.92 times that of Compound 7. The spin-evaporated product was added with ethanol (1.59 L) and slurried at 75±5° C. for 15-16 hours. The solution after slurrying was cooled down to 25±5° C. and filtered, and the obtained filter cake was collected and spin-evaporated at 45±5° C. to a weight that is 0.87-0.9 times that of Compound 7. The spin-evaporated product was added with water (2.35 L) and stirred at 45±5° C. for 61±1 hours. The mixed solution was cooled down to 25±5° C. and filtered. The obtained filter cake was collected, added with water (2.35 L), stirred at 25±5° C. for 2-3 hours and filtered. The obtained filter cake was collected, vacuum-dried at 60° C. for 15-16 hours and then sieving over a 60 mesh sieve, to give a light yellow solid product (190 g, 98.33% purity, 47.36% yield).

$^1$H NMR (400 MHz, DMSO-d6-d) d=2.96 (t, J=6.0 Hz, 2H), 3.72 (s, 3H), 4.27 (t, J=5.2 Hz, 2H), 7.32 (td, J=8.8, 2.8 Hz, 1H), 7.60 (dd, J=8.4, 2.4 Hz, 1H), 7.70 (d, J=9.2 Hz, 1H), 7.75 (d, J=2.0 Hz, 1H), 7.95-8.05 (m, 2H), 8.15 (d, J=1.6 Hz, 1H), 8.27 (s, 1H), 8.85 (s, 1H); LCMS (ESI) m/z: 548 (M+1).

Example 2: Preparation of Crystalline Form IX of Compound 1

7-(5-amino-6-methoxypyrimidin-3-yl)-3-(2-(dimethylamino)ethoxy)-pyrido[1,2-a]pyrimidin-4-one (2.5 g, 6.75 mmol, 1.0 eq) was dissolved in pyridine (25 mL), added dropwise with 2-chloro-4-fluorobenzenesulfonyl chloride (2.01 g, 8.78 mmol, 1.3 eq) at 0° C. and stirred at 10° C.-20° C. for 16 hours. After the reaction was completed, the solvent was spin-dried out to give a crude product. The crude product was purified by a column (DCM/MeOH: 10/1-4/1). A yellow solid product was obtained (2.4 g, 98.31% purity, 63.79% yield). The above yellow solid (1.3 g, 2.37 mmol) was separated by preparative HPLC (neutral). The liquid from separation with preparative HPLC (neutral) was extracted with DCM (500 mL×3). The organic phase was dried over anhydrous sodium sulfate (100 g) and then filtered, and the obtained filtrate was spin-dried to give a white solid product, crystalline Form IX of Compound 1 (970 mg, 1.75 mmol, 99% purity, 73.94% yield).

Example 3: Preparation of Crystalline Form I of Compound 2

7-(5-amino-6-methoxypyrimidin-3-yl)-3-(2-(dimethylamino)ethoxy)-pyrido[1,2-a]pyrimidin-4-one (29.0 g, 81.60 mmol, 1.0 eq) and pyridine (290 mL) was added in a 1.0 L three-necked round-bottomed flask R1 equipped with a stirrer. R1 was placed in an ice bath and cooled down to 0-5° C. A solution of 2-chloro-4-fluorobenzenesulfonyl chloride (24.30 g, 106.08 mmol, 1.3 eq) in pyridine (60 mL) was added dropwise in R1, which took about 30 min, and the reaction solution was naturally warmed up to 20° C. and reacted with stirring for 16 hours. After the reaction was completed, the reaction solution was concentrated under reduced pressure to remove pyridine, to give 80 g of a red solid crude product. 64 g of the above crude product was taken and placed in a 1.0 L round-bottomed flask R2, and dichloromethane (350 mL) was added in R2. R2 was then stirred at 15° C. for 2 hours and filtered, and the obtained filter cake was collected and dried to give a light red solid (33.4 g, 77% yield, 99.4% purity). 30 g of the above solid was taken and placed in a 1 L round-bottomed flask R3, and methanol (600 mL) and activated carbon (6 g, 20%) were added in R3. The mixture was placed in an oil bath at 70° C. and stirred for 12 hours. The mixture was filtered with diatomaceous earth (15 g) when it was hot. The filtrate was collected and spin-dried to give a yellow solid product (22.6 g, 97.47% purity). Acetonitrile (150 mL) was added to the above solid; the resulting mixture was stirred in an oil bath at 85° C. for 12 hours, cooled down to 20° C. and filtered; and the filter cake was collected and dried to give the titled product as a white solid, crystalline Form I of Compound 2 (21 g, 44.3% yield, 100% purity). The molar ratio of chloride ion of Compound 2 to that of Compound 1 was 1:1 as determined by ion chromatography.

$^1$H NMR (400 MHz, DMSO-d6-d) d=2.91 (s, 6H), 3.53 (t, 2H), 3.71 (s, 3H), 4.52 (t, 2H), 7.38 (m, 1H), 7.77 (m, 2H), 7.97 (m, 2H), 8.16 (m, 1H), 8.45 (m, 2H), 8.98 (s, 1H).

Example 4: Preparation of Crystalline Form II of Compound 2

About 50 mg of crystalline Form I of Compound 2 was taken and added with 0.4 mL acetone to form a suspension. The suspension sample was placed on a mixer at a constant temperature (40° C.) and shaken for 2 days (protected from light). The residual solid were centrifuged and dried in a vacuum drying oven at 40° C. overnight, to give crystalline Form II of Compound 2.

Example 5: Preparation of Crystalline Form III of Compound 2

The preparation procedure of crystalline Form III is identical to that of crystalline Form II, except that the solvent of acetone is replaced with isopropanol. Crystalline Form III of Compound 2 was obtained.

Example 6: Preparation of Crystalline Form IV of Compound 2

The preparation procedure of crystalline Form IV is identical to that of crystalline Form II, except that only the solvent of acetone is replaced with ethyl acetate. Crystalline Form IV of Compound 2 was obtained.

Example 7: Preparation of Crystalline Form V of Compound 2

Crystalline Form I of Compound 2 (2.0 g, 3.42 mmol) was placed in a 500 mL single-necked flask R1, and the solid was completely dissolved by adding DCM/MeOH (2/1, 200 mL) with stirring. The solution was subjected to a reduced pressure at 40° C. to remove the solvent, to give 2.0 g of a yellow solid; 1 g of the solid was taken and placed in a 50 mL single-necked flask, followed by adding ethanol (6 mL); and the obtained mixture was placed in an oil bath at 80° C. with stirring for 12 hours, and then the heating was stopped. The mixture was cooled down to 20° C. under stirring and then filtered, and the filter cake was dried, to give crystalline Form V of Compound 2.

Example 7: Preparation of Crystalline Form VI of Compound 2

7-(5-amino-6-methoxypyrimidin-3-yl)-3-(2-(dimethylamino)ethoxy)-pyrido[1,2-a]pyrimidin-4-one (70.0 g, 222.90 mmol, 1.0 eq, 99.4% purity) and pyridine (700 mL) were added in a 2.0 L three-necked round-bottomed flask R1 equipped with a mechanical stirrer, and R1 was placed in an ice bath and cooled down to 0-5° C. A solution of 2-chloro-4-fluorobenzenesulfonyl chloride (70.81 g, 293.67 mmol, 1.5 eq, 95% purity) in pyridine (140 mL) was added dropwise in R1, which took about 30 min. R1 was placed in an oil bath at 30° C. and reacted with stirring for 2 hours. After the reaction was completed, the reaction solution was concentrated under reduced pressure to remove the solvent pyridine, to give a red solid crude product (200 g). The residue was added with dichloromethane (1.0 L) and stirred at 20° C. for 3 hours. After filtration, the filter cake was collected. Acetonitrile (1.2 L) was added to the filter cake; the obtained reaction solution was refluxed at 85° C. for 12 hours, cooled down to 20° C. and filtrated; and another filter cake was collected and dried to give a solid (92 g). The solid of the filter cake was added with methanol (2 L) and activated carbon (14 g), refluxed with stirring for 3 hours, filtrated with diatomaceous earth (40 g) when it still was hot, and rinsed with 500 mL. The filtrate was spin-dried under reduced pressure at 40° C. to give a solid (83 g). The obtained solid was added with acetonitrile (800 mL), and the mixture was refluxed at 85° C. overnight, cooled down to 20° C. and filtrated, and the resulting filter cake was dried to give 77 g of a white solid. 72 g of the white solid was taken and completely dissolved in methanol and spin-dried, to give crystalline Form VI of Compound 2.

Example 8: Preparation of Crystalline Form VII of Compound 3

Compound 1 (997.34 mg, 1.82 mmol, 1.00 eq) was placed in a 5 mL glass vial, added with ethanol/water (7.5 mL/2.5 mL), and stirred at room temperature (15° C.) for 0.1 hours, in which a large amount of solid was not dissolved. Maleic acid (211.25 mg, 1.82 mmol, 1.00 eq) was added to the mixture and stirred at room temperature (15° C.) for 18 hours, and the solid was allowed to be completely dissolved and formed a yellow solution. The obtained solution was spin-dried under reduced pressure at 40° C. to the volume of 2 mL, added with EA (20 mL), stirred for 0.5 hours, and filtered; the formed filter cake was spin-dried under reduced pressure at 40° C. to give crystalline Form VII of Compound 3.

$^1$H NMR (400 MHz, DMSO-$d_6$) d ppm 2.94 (s, 6H) 3.51-3.56 (m, 2H) 3.71 (s, 3H) 4.36-4.59 (m, 2H) 6.03 (s, 2H) 7.18-7.48 (m, 1H) 7.65-7.90 (m, 2H) 7.92-8.09 (m, 2H) 8.17 (dd, J=9.29, 1.76 Hz, 1H) 8.35-8.55 (m, 2H) 8.99 (s, 1H).

Example 9: Preparation of Crystalline Form VIII of Compound 4

Compound 1 (997.34 mg, 1.82 mmol, 1.00 eq) was placed in a 5 mL glass vial, added with ethanol/water (7.5 mL/2.5 mL), and stirred at room temperature (15° C.) for 0.5 hours, in which a large amount of solid was not dissolved. Citric acid (382.45 mg, 1.82 mmol, 1.00 eq) was added to the mixture and stirred at room temperature (15° C.) for 18 hours to give a milky white slurry in the reaction vial. The mixed solution obtained was spin-dried under reduced pressure at 40° C. to the volume of 2 mL, added with EA (20 mL), stirred for 0.5 hours and filtered; the formed filter cake was spin-dried under reduced pressure at 40° C. to give crystalline Form VIII of Compound 4.

$^1$H NMR (400 MHz, DMSO-$d_6$) d ppm 2.56-2.68 (m, 4H) 2.76 (s, 6H) 3.31 (m, 2H) 3.72 (s, 3H) 4.37-4.40 (m, 2H) 7.35-7.37 (m, 1H) 7.71-7.78 (m, 2H) 7.91-7.95 (m, 1H) 7.95-8.09 (m, 1H) 8.11-8.13 (m, 1H) 8.36-8.37 (m, 2H) 8.96 (d, J=1.6, 1H).

Test Example 1: Test of Stability of Crystalline Form IX of Compound 1 in Different Solvents Several samples of crystalline Form IX of Compound 1 in a suitable amount were taken, respectively added to 0.3-0.4 mL of a single solvent or a mixed solvent as shown in the following table, and stirred at 40° C. After stirring for 2 days, the samples were centrifuged. Solid in the samples was collected and its crystalline state was detected by XRPD. The results were shown in Table 10.

TABLE 10

Stability experiments of crystalline Form IX of the free base form in different solvents

| Nos. | Solvents | Appearance (2 days) | Results |
|---|---|---|---|
| 1 | methanol | suspension | crystalline Form IX |
| 2 | ethanol | suspension | crystalline Form IX |
| 3 | isopropanol | suspension | crystalline Form IX |
| 4 | acetone | suspension | crystalline Form IX |
| 5 | acetonitrile | suspension | crystalline Form IX |
| 6 | tetrahydrofuran | suspension | crystalline Form IX |
| 7 | ethyl acetate | suspension | crystalline Form IX |
| 8 | methanol-water (3:1) | suspension | crystalline Form IX |
| 9 | ethanol-water (3:1) | suspension | crystalline Form IX |
| 10 | acetone-water (1:2) | suspension | crystalline Form IX |
| 11 | isopropanol-water (1:1) | suspension | crystalline Form IX |

Test Example 2: Test of Solid State Stability of Crystalline Form IX of Compound 1 Under Conditions of High Temperature, High Humidity and Strong Light About 10 mg of crystalline Form IX of Compound 1 was weighed and placed on a bottom of a glass sample bottle to form a thin layer. For the samples placed under the conditions of 60° C. and room temperature/92.5% RH, the top of the bottles was covered with aluminum foil, and several holes were made in aluminum foil, which is ensure that the samples were fully exposed to the air in the environment; for the samples placed under strong light (5 Klx), the bottles were sealed with a screw cap. Another sample of 15 mg of crystalline Form IX was taken and placed according to the method as described above for detecting the crystalline form of the sample. The samples placed under different conditions were sampled and detected on day 5 and day 10, and the detection results were compared with the initial detection results on day 0. The test results were shown in Table 11 below.

TABLE 11

Solid state stability test of crystalline Form IX of Compound 1

| Test conditions | Time point (day) | Appearance | Crystalline Form | Content (%) | Total impurities (%) |
|---|---|---|---|---|---|
| — | 0 | White powder | crystalline Form IX | 101.02 | 0.32 |
| High temperature 60° C. (opened) | 5 | White powder | crystalline Form IX | 100.64 | 0.32 |
| | 10 | | | 100.55 | 0.33 |
| Room temperature/ 92.5% RH (opened) | 5 | White powder | crystalline Form IX | 101.05 | 0.32 |
| | 10 | | | 101.16 | 0.32 |
| Light 5KIx (closed) | 5 | White powder | crystalline Form IX | 100.43 | 0.31 |
| | 10 | | | 101.10 | 0.32 |

Experimental results: the crystalline forms of the present invention have good stability, and can be easily manufactured to a medicament.

Test Example 3: In Vitro Tests of Enzyme Activity

ADP-Glo Assay I

Compound Dilution:

The test compounds were diluted with a three-fold concentration gradient, and 10 concentrations (10000 nM to 0.5 nM) were obtained in total.

Experimental Method:

50 nL of the test compounds of the present invention was transferred to a reaction plate (PerkinElmer #6007299), and added with 3 μL of an enzyme/substrate mixture (0.33 nM PI3Kalpha, Millipore #14-602-K/166.5 μM PIP2); after incubation for 20 min, 2 μL of an ATP solution (100 μM) was added to initiate the reaction; after 2 hours of reaction at room temperature, the kinase reaction was stopped by adding 5 μL ADP-Glo reagent, followed by incubation at room temperature for 60 min, allowing the remaining unreacted ATP to be completely digested; and the resulting solution was added with 10 μL of a kinase detection reagent and incubated at room temperature for 40 min, and then the fluorescence was read on Envision. PIP2, ATP, the ADP-Glo reagent, and the kinase assay reagents are all from an ADP-Glo Kinase Assay Kit (Promega #V1792).

Data Analysis:

$IC_{50}$ was calculated using the standard 4-parameter fitting method (Model 205, XL-fit, iDBS).

The activity of the test compounds of the present invention on mTOR kinase was tested by the test method below.

Reaction Buffer: 20 mM Hepes (pH 7.5), 10 mM $MgCl_2$, 2 mM $MnCl_2$, 1 mM EGTA, 0.02% Brij35, 0.02 mg/mL BSA, 0.1 mM $Na_3VO_4$, 2 mM DTT, 2% DMSO.

Enzyme for reaction: humanized recombinant mTOR fragment with a N-terminal GST tag (amino acid 1360-2549, molecular weight=163.9 kDa), expressed in insect cells.

Reaction Substrate: humanized recombinant full-length 4EBP1 with a N-terminal His tag (molecular weight=13.6 kDa), expressed in bacteria;

Reaction conditions: 3 μM 4EBP1 and 10 μM ATP.

Reaction Procedure:

1. The reaction substrate and other reaction factors were added to the freshly prepared reaction buffer.
2. The kinase was added to the substrate reaction and gently mixed.
3. The compound dissolved in 100% DMSO was transferred into the kinase reaction solution using Acoustic technology (Echo 550; nanoliter rang) and then incubated at room temperature for 20 min.
4. An appropriate concentration of $^{32}$P-ATP was add to the reaction system.
5. It was incubated at room temperature for 2 hours.
6. Kinase activity was detected by the P81 filter-binding method.

The experimental results were shown in Table 12.

TABLE 12 test results of in vitro enzyme activity

| Compound | $IC_{50}$ of PI3K (p110α) enzyme activity | $IC_{50}$ of mTOR enzyme activity |
|---|---|---|
| Compound 1 | A | D |

Note:
A ≤ 1 nM; 200 nM < D.

Conclusion: Compound 1 has a significant inhibitory effect on PI3K (p110α), but its inhibitory effect on mTOR is weaker.

ADP-Glo Assay II

Experimental Procedure:

1) The compound was diluted using Echo from Labcyte company, 50 nL of the compound was transferred into an assay plate, and centrifuged at a speed of 1000 rpm for 10 sec.

2) A kinase/lipid substrate mixed solution and a kinase reaction buffer/lipid substrate mixed solution were prepared; the kinase/lipid substrate mixed solution was added into columns 3-24 of the assay plate, 3 μL per well; the kinase reaction buffer/lipid substrate mixed solution was added into columns 1-2 of the assay plat, 3 μL per well; and the plate was centrifuged at a speed of 1000 rpm for 10 sec.

3) An ATP solution was prepared, and added into the assay plate, 2 μL per well; the plate was centrifuged at a speed of 1000 rpm for 10 sec, shaken and mixed in 2nd gear mode on a plate shaker for 1 min, further centrifuged at a speed of 1000 rpm for 10 sec, and incubated for 120 min at 23° C.

4) An ADP-Glo® reagent was prepared, and added into the assay plate, 5 μL per well; the plate was centrifuged at a speed of 1000 rpm for 10 sec, shaken and mixed in 2nd gear mode on a plate shaker for 1 min, further centrifuged at a speed of 1000 rpm for 10 sec, and incubated for 60 min at 23° C.

5) A kinase detection reagent was prepared, added into the assay plate, 10 µL per well; the plate was centrifuged at a speed of 1000 rpm for 10 sec, shaken and mixed in 2nd gear mode on a plate shaker for 1 min, further centrifuged at a speed of 1000 rpm for 10 sec, incubated for 30 min at 23° C.; and then read on the multi-marker detector Envision.

Data Analysis:

IC$_{50}$ results were analyzed by XLfit5 (Formula 205) of IDBS company.

The corresponding experiments and analysis were performed by employing the experimental procedure as described above, with Compound BKM-120 as a positive control drug.

Experimental Results:

IC$_{50}$ values for inhibition of Compound 1 on PI3Kα, PI3Kβ, PI3Kδ, and PI3Kγ activity were respectively 0.6±0.2 nM, 9.9±2.7 nM, 0.5±0.1 nM, and 7.0±0.9 nM (n=2). In contrast, IC$_{50}$ values for inhibition of the positive control drug BKM120 (PI3K inhibitor, Buparlisib) on PI3Kα, PI1Kα, PI3Kδ, and PI3Kγ activity were 24.7±4.7 nM, 241.6±50.6 nM, 68.8±25.0 nM, and 111.9±15.2 nM, respectively.

Conclusion: Compound 1 exhibits very high inhibitory activity on all four subtypes of PI3K.

Test Example 4: In Vitro Tests of Cell Activity

Experimental Steps and Methods:

1) MCF-7 cells were inoculated at the density of 2.5×10$^4$ cells/well into 96-well plates (the culture medium used should be a complete culture medium containing 10% FBS).

2) On the next day, the medium in each well was drawn out. A certain concentration (preliminary screening) or a series of concentration (IC$_{50}$ test) of test compounds were dissolved in a culture medium without serum and added to the 96-well plates to culture cells for 2 hours.

3) Insulin was dissolved in a culture medium without serum, added to the cultured cells and incubated for 30 minutes, wherein the final concentration of insulin was 10 mg/mL.

4) A lysis solution was prepared according to the following method during the waiting period for the reaction:
  a) Enhancer solution was removed from the refrigerator to melt in advance.
  b) Enhancer solution was diluted 10-fold with the 5× Lysis Buffer to give a concentrated lysis solution.
  c) The concentrated lysis solution was diluted 5-fold with double distilled water to give the lysis solution.

5) The medium in each well was completely removed and each well was quickly rinsed with PBS once.

6) 150 µL of the freshly prepared lysis solution was added to each well and shaken at room temperature for 10 min.

7) After confirming that all cells were detached, the lysis solution together with cell debris was transferred into a 1.5 mL tube.

8) The tube was vortexed several times, allowing the lysis solution and cells to mix completely, and then the mixture was centrifuged at 4° C., under 12000 g for 10 min.

9) The number of strips of ELISA-one micro-well plate that is required was calculated. The needless strips were removed from the frame, put back into the storage bag and sealed. Before the strips of micro-well plate were used, 200 µL of double distilled water was used to rinse each well to remove preservative.

10) 50 µL of antibody mixture was added to each well. (The antibody mixture solution was prepared by mixing the medium antibody reagent and the enzyme labeled antibody reagent with an equal proportion. The preparation of antibody mixture didn't need vortex.)

11) 25 µL of cell lysates was added to each well of ELISA-One micro-well plate. The micro-well plate was covered with adhesive sealing film and incubated on a micro-well plate oscillation instrument at room temperature for 1 hour.

12) Each well was rinsed with 150 µL of 1× rinsing buffer 3 times. After the last rinsing, the rinsing buffer in the well was completely removed. If necessary, the 1× rinsing buffer could be allowed to stay in the micro-well plate for up to 30 min so that the substrate mixed solution could be prepared during such time period.

13) The substrate mixed solution should be prepared just before each use, 100 µl of the substrate mixed solution was added to each well and the micro-well plate was sealed with tin-foil and incubated on the micro-well plate oscillation instrument at room temperature for 10 min.

14) 10 µL of stop solution was added to each well and mixed slightly (5-10 sec) on the micro-well plate oscillation instrument.

15) The corresponding ELISA-One filter group was assembled and used to read the fluorescence signal intensity.

The experimental results are shown in Table 13.

TABLE 13

| Test results of in vitro cell activity | |
| --- | --- |
| Compound | IC$_{50}$ of cell activity |
| Compound 1 | A |

Note:
A ≤ 50 nM.

Test Example 5: In Vivo Efficacy Experiment

The studies were conducted to examine if the test drugs have in vivo efficacy in the human colon cancer CO-04-0032 animal model and the gastric cancer ST-02-0013 animal model. The descriptions about the animal feeding, feed ingredients, experimental observation, experimental indexes, experimental termination, as well as data analysis in the tests were as follows:

Animal Feeding: Upon arrival, animals should be fed in the experimental environment for 3-7 days before starting the experiment. The animals were housed in IVC (independent ventilation system) cages (5 animals per cage) in SPF-grade animal houses. All cages, padding, and drinking water were required to be sterilized before use, and the sterilization records were shown in the annex. All laboratory personnel in animal houses should wear protective clothing and latex gloves when operating. Each cage information card of should indicate the number of animals in the cage, gender, strain, arrival date, dosage regimen, experiment number, group, and date of commencement of experiments. Cages, feed and drinking water were replaced twice a week.

Feeding environment and light conditions are as follows:
temperature: 20~26° C.
humidity: 40~70%
light and dark cycle: 12 h with light, 12 h without light Feed Ingredients: Feed conformed to the laboratory animal food identification standard. The maximum content of pollutants is within the controllable range and the manufacturer is responsible for routine inspection. Autoclaved drinking water was used as drinking water.

Animal Grouping: The animals were weighed and the tumor volume was measured prior to administration. The animals were randomly grouped according to tumor volume (randomized block design).

Observation: The experimental protocol and any modifications thereof were conducted with the approval of the Institutional Animal Care and Use Committee (IACUC) of WuXi AppTec, Shanghai. The use and welfare of experimental animals followed the rules of the Association for Assessment and Accreditation of Laboratory Animal Care (AAALAC). The animal health and death were monitored daily, and routine examinations include observing tumor growth and influences of treatment with drug on animals' daily behavior and performance such as behavior, food and water intake, body weight change (with body weight measurements twice a week), appearance or other abnormal situation. Animal deaths and side effects were recorded based on the number of the animals in each group, and the correlated records can be seen in the appendix.

Experimental Indexes: The experimental indexes were used to examine whether tumor growth is inhibited, delayed or cured. Tumor diameter was measured twice a week with a vernier caliper. The tumor volume was calculated by the formula: $V=0.5 \times a \times b^2$, wherein a and b represent the long diameter and short diameter of a tumor, respectively. Tumor growth inhibition (TGI) of a compound was evaluated with T-C (day) and T/C (%). The T-C (day) reflects tumor growth delay index, wherein T represents the average number of days required for reaching a predetermined tumor volume (eg, 1,000 mm$^3$) in an administration group, and C represents the average number of days required for reaching the same tumor volume in a control group. The percentage value of T/C (%) reflects tumor growth inhibition rate, wherein T and C represent tumor weight (tumor volume) in the administration group and a control group on a certain day, respectively.

Tumor growth inhibition rate was calculated by the following formula: TGI (%)=$[1-(T_i-T_0)/(V_i-V_0)] \times 100$, wherein $T_i$ is average tumor volume of the administration group on a certain day, and $T_0$ is average tumor volume of the administration group at the beginning of administration; $V_i$ is average tumor volume of a vehicle control group on the certain day (the same day as $T_i$), and $V_0$ is average tumor volume of the vehicle control group at the beginning of administration. At the end of the experiment, the tumor weight was measured and the T/C percentage was calculated, wherein T and C represent the tumor weight of the administration group and the vehicle control group, respectively.

Experiment Termination: If the health condition of an animal continues to deteriorate or an animal has more than 2,000 mm$^3$ of the tumor volume, or serious illness or pain, the animal must be euthanized. If the following conditions appear, a veterinarian would be notified and animals are euthanized:

Obviously thin, weight loss of greater than 20%;
Being unable to free access to food and water;
Average tumor volume of a control group reaching 2,000 mm$^3$, in which case the experiment should be terminated.

An Animal has the following clinical manifestations and they continue to deteriorate:
Piloerection
Arched back
Pale ear, nose, eye or foot
Breathing hastily
Seizures
Persistent diarrhea
Dehydration
Slow movement
Sound Data Analysis: One-way ANOVA was used for comparison of three or more groups. If there is a significant difference in F values, multiple comparisons should be performed after ANOVA analysis. All data was analyzed using SPSS 17.0. $p<0.05$ indicated a significant difference.

In Vivo Pharmacodynamics Studies of Test Drugs in Subcutaneous Xenograft Tumor Models of Human Colon Cancer CO-04-0032 Cells:

Experimental Design:

Establishment of human tumor transplantation model: The human colon cancer CO-04-0032 model was originally derived from tumor specimens removed in surgery. Acquisition and use of the specimens strictly complied with the ethical laws and regulations of nation, hospitals and companies, including informed consent from the patient. The process for establishing the model strictly followed the company's internal SOP. The rules for naming the passage generation was as follows: the tumor after inoculation of the tumor specimen in a nude mouse was designated generation P0, the continued passage was designated generation P1, and so on; and the revived specimen was designated FP. The tumor tissues used in this experiment were generation FP4.

Animals: BALB/c nude mice, female, 6-8 weeks old, 18-20 g of body weight, provided by Shanghai Sippr-BK Laboratory Animal Co., Ltd.

Tumor inoculation: A volume of around 30 mm$^3$ of CO-04-0032 tumor mass was inoculated subcutaneously into the right back of each mouse; and the mice were divided into groups and drugs were administered to each group, when the average tumor volume reached approximately 100 to 200 mm$^3$.

Experimental Results: there is almost no increase in tumor volume from day 15 to day 30 of the administration of Compound 1 (comprising crystalline Form IX thereof) of the present invention; and compared to the positive control drug BKM120, Compound 1 (comprising crystalline Form IX thereof) of the present invention has a more excellent anti-tumor activity for colon cancer.

In Vivo Pharmacodynamics Studies of Test Drugs in Subcutaneous Xenograft Tumor Model of Human Gastric Cancer ST-02-0013

Experimental Design:

Establishment of human tumor transplantation model: The PDX model of the ST-02-0013 was originally derived from a clinical specimen removed by surgery, which was implanted into the nude mice and designated generation P0. The next generation from implantation with P0 tumors was designated generation P1, and so on for the tumors by continuous implantation from generation to generation in mice. FP2 tumors were revived to obtain FP3 tumors. FP3 tumors were passaged to obtain FP4 tumors, which were used for this study.

Animals: BALB/c nude mice, female, 6-8 weeks old, 18-22 g of body weight, provided by Shanghai Ling Chang Biotechnology Co., Ltd.

Tumor inoculation: A volume of around 30 mm$^3$ of ST-02-0013 FP4 tumor tissue was inoculated subcutaneously into the right back of each mouse; and the mice were divided into groups and drugs were administered to each group, when the average tumor volume reached approximately 150 to 200 mm$^3$.

Experimental Results: there is almost no increase in tumor volume from day 15 to day 30 of the administration of Compound 1 (comprising crystalline Form IX thereof) of the present invention; and compared to the positive control drug BKM120, Compound 1 (comprising crystalline Form IX thereof) of the present invention has a more excellent anti-tumor activity for gastric cancer.

What is claimed is:

1. Crystalline forms of Compound 1 as represented by the following formula or salts thereof, wherein crystalline Forms of Compound 1 or the salts thereof are selected from the group consisting of Crystalline Forms I, II, III, IV, V, VI, VII, VIII and IX:

Compound 1

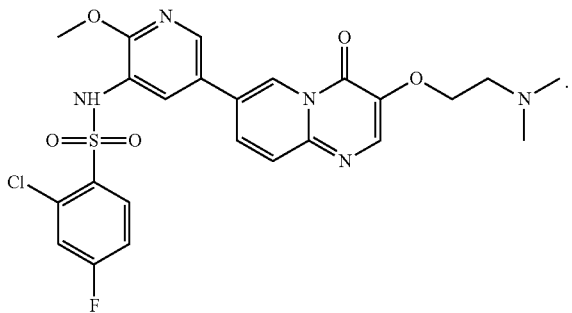

2. Crystalline forms of Compound 1 or the salts thereof of claim 1, characterized in that crystalline Form IX of Compound 1 has diffraction peaks at 2θ=7.947°, 10.073°, 14.531°, 19.187°, 21.237°, 24.055°, 25.497° in a X-ray diffraction pattern.

3. Crystalline forms of Compound 1 or the salts thereof of claim 2, characterized in that XRPD pattern analysis data of crystalline Form IX is as follows:

| Nos. | 2θ degree | Relative intensity % |
|---|---|---|
| 1 | 6.014 | 2.5 |
| 2 | 7.947 | 29.0 |
| 3 | 10.073 | 54.2 |
| 4 | 11.970 | 23.3 |
| 5 | 13.053 | 5.9 |
| 6 | 13.468 | 14.4 |
| 7 | 14.531 | 62.5 |
| 8 | 14.828 | 49.7 |
| 9 | 15.911 | 31.1 |
| 10 | 17.369 | 21.8 |
| 11 | 17.569 | 26.1 |
| 12 | 17.941 | 4.5 |
| 13 | 18.377 | 1.6 |
| 14 | 19.187 | 55.2 |
| 15 | 19.561 | 41.3 |
| 16 | 19.855 | 61.5 |
| 17 | 20.233 | 22.2 |
| 18 | 21.237 | 62.8 |
| 19 | 21.984 | 22.0 |
| 20 | 22.373 | 3.2 |
| 21 | 23.073 | 2.2 |
| 22 | 23.446 | 32.9 |
| 23 | 24.055 | 100.0 |
| 24 | 24.847 | 6.6 |
| 25 | 75.497 | 60.4 |
| 26 | 26.265 | 1.3 |
| 27 | 27.074 | 28.0 |
| 28 | 27.448 | 10.1 |
| 29 | 27.862 | 22.8 |
| 30 | 28.081 | 15.6 |
| 31 | 29.005 | 4.5 |
| 32 | 29.445 | 3.3 |
| 33 | 30.171 | 13.0 |
| 34 | 31.014 | 1.5 |
| 35 | 31.437 | 0.7 |
| 36 | 31.963 | 19.5 |
| 37 | 32.381 | 23.5 |
| 38 | 33.937 | 9.1 |
| 39 | 34.565 | 4.7 |
| 40 | 35.218 | 6.8 |
| 41 | 36.403 | 5.8 |
| 42 | 36.897 | 3.7 |
| 43 | 38.103 | 7.1 |
| 44 | 38.605 | 6.8 |
| 45 | 39.502 | 2.6. |

4. Crystalline forms of Compound 1 or the salts thereof of claim 2, characterized in that a XRPD pattern of crystalline Form IX is as shown in FIG. 25.

5. Crystalline forms of Compound 1 or the salts thereof of claim 1, wherein the salt is represented by the following formula Compound 2, Compound 2

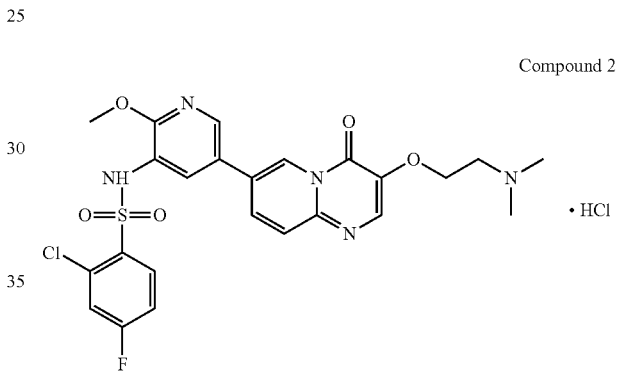

characterized in that crystalline Form I of Compound 2 has diffraction peaks at 2θ=10.1540°, 12.285°, 14.511°, 16.328°, 24.311°, 26.188° in a X-ray diffraction pattern.

6. Crystalline forms of Compound 1 or the salts thereof of claim 1, wherein the salt is represented by the following formula Compound 2, Compound 2

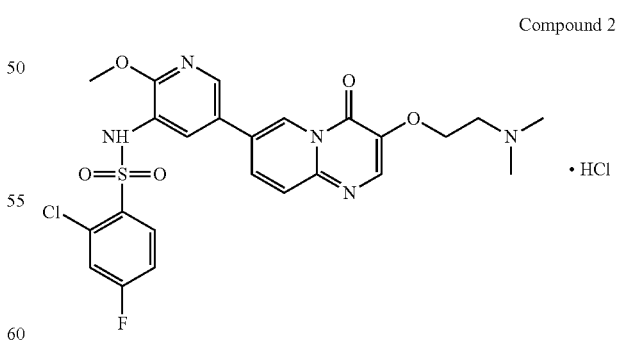

characterized in that crystalline Form II of Compound 2 has diffraction peaks at 2θ=6.524°, 7.782°, 13.895°, 15.495°, 17.487°, 19.322° in a X-ray diffraction pattern.

7. Crystalline forms of Compound 1 or the salts thereof of claim 1, wherein the salt is represented by the following formula Compound 2, Compound 2

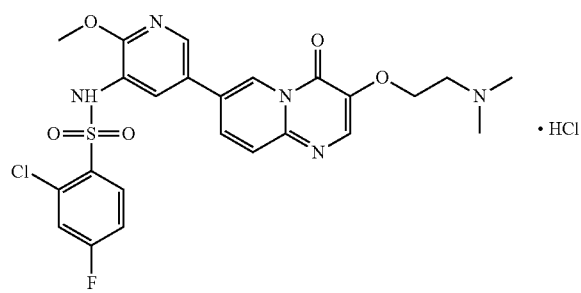

characterized in that crystalline Form III of Compound 2 has diffraction peaks at 2θ=6.979°, 9.939°, 14.392°, 16.107°, 20.982°, 25.990° in a X-ray diffraction pattern.

8. Crystalline forms of Compound 1 or the salts thereof of claim 1, wherein the salt is represented by the following formula Compound 2, Compound 2

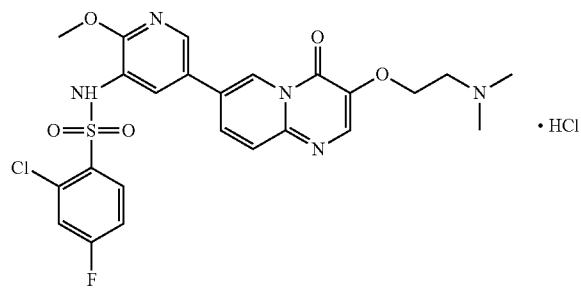

characterized in that crystalline Form IV of Compound 2 has diffraction peaks at 2θ=6.388°, 7.278°, 11.076°, 15.454°, 21.256° in a X-ray diffraction pattern.

9. Crystalline forms of Compound 1 or the salts thereof of claim 1, wherein the salt is represented by the following formula Compound 2, Compound 2

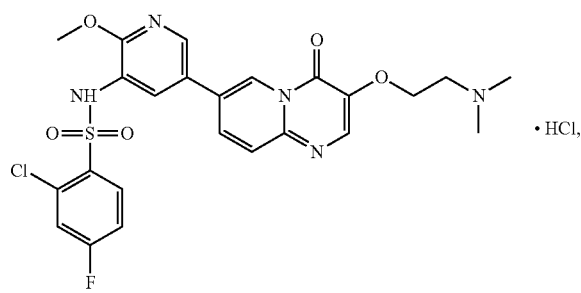

characterized in that crystalline Form V of Compound 2 has diffraction peaks at 2θ=7.116°, 14.137°, 15.911°, 22.223°, 24.610° in a X-ray diffraction pattern.

10. Crystalline forms of Compound 1 or the salts thereof of claim 1, wherein the salt is represented by the following formula Compound 2, Compound 2

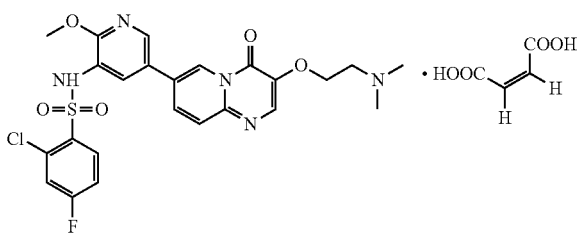

characterized in that crystalline Form VI of Compound 2 has diffraction peaks at 2θ=5.775°, 11.77°, 14.415°, 15.753°, 22.518°, 26.623° in a X-ray diffraction pattern.

11. Crystalline forms of Compound 1 or the salts thereof of claim 1, wherein the salt is represented by the following formula Compound 3, Compound 3 characterized in that crystalline Form VII of Compound 3 has diffraction peaks at 2θ=6.325°, 12.677°, 15.813°, 21.395°, 22.519°, 27.133° in a X-ray diffraction pattern.

12. Crystalline forms of Compound 1 or the salts thereof of claim 1, wherein the salt is represented by the following formula Compound 4,

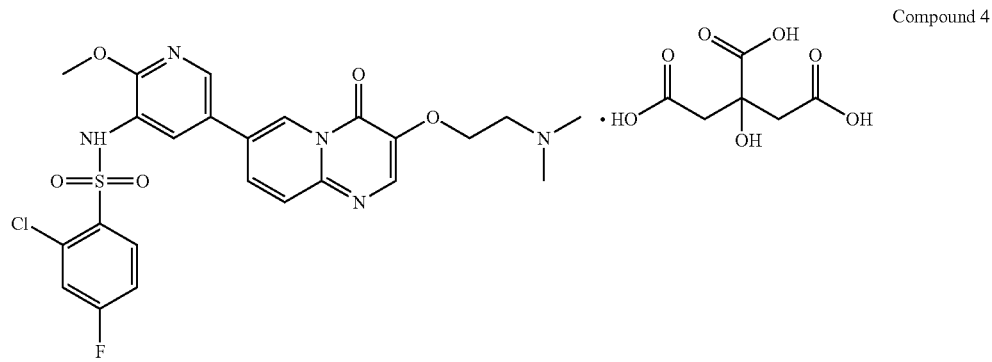

Compound 4 characterized in that crystalline Form VIII of Compound 4 has diffraction peaks at 2θ=5.889°, 11.002°, 12.518°, 14.906°·17.825°, 22.814°, 25.555° in a X-ray diffraction pattern.

13. A pharmaceutical composition comprising crystalline forms of Compound 1 or the salts thereof of claim 1, wherein the pharmaceutical composition comprises a therapeutically effective amount of the crystalline forms, and optionally pharmaceutically acceptable carriers, excipients and/or media.

14. A method for treating colon cancer and/or gastric cancer, comprising administering a therapeutically effective amount of crystalline forms of Compound 1 or the salts thereof of claim 1 to patients in need.

15. A method for preparing Compound 1 as represented by the following formula,

Compound 1

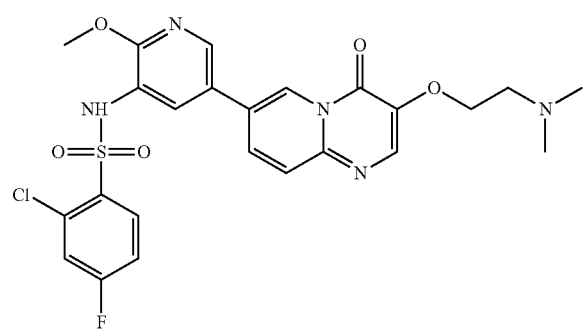

comprising the following steps,

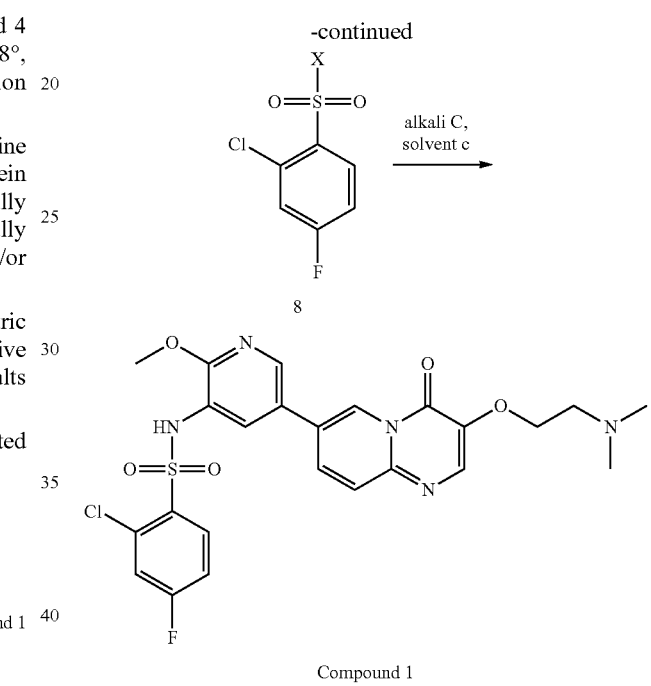

Compound 1 wherein

X is selected from Cl or Br;

alkali C is selected from pyridine, 2,6-lutidine, Et₃N, 4-DMAP, LiOH, Cs₂CO₃, or K₂CO₃;

solvent c is selected from pyridine, dichloromethane, toluene, acetonitrile, acetone, DMF or THF;

a molar ratio of Compound 7 to Compound 8 is 1:1-3;

a molar ratio of Compound 7 to alkali C is 1:1~3.

16. The method of claim 15, the method comprises the following steps,

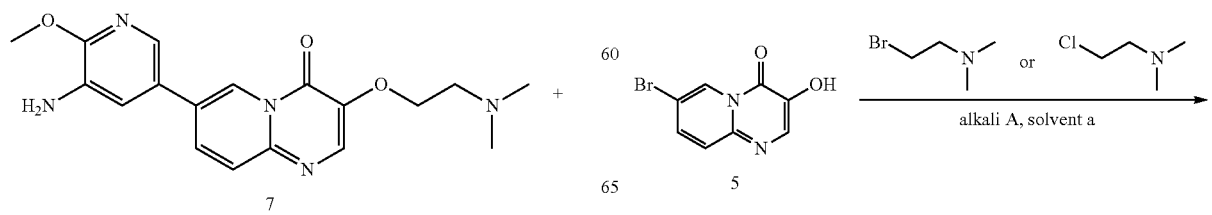

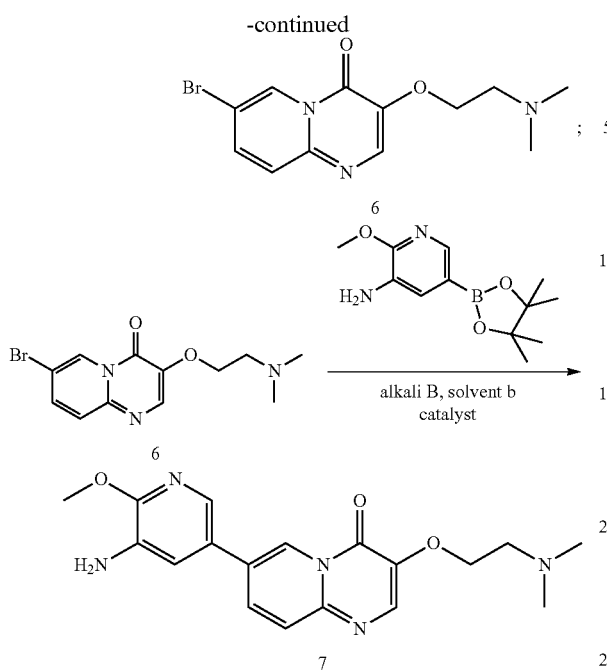

wherein alkali A is selected from potassium carbonate, sodium carbonate, cesium carbonate, potassium hydroxide, or sodium hydroxide;

solvent a is selected from DMF, DMSO, or NMP;

alkali B is selected from potassium carbonate, sodium carbonate, barium hydroxide, potassium phosphate, cesium carbonate, potassium fluoride, cesium fluoride, sodium hydroxide, potassium t-butoxide, sodium t-butoxide, potassium acetate or sodium acetate;

solvent b is selected from 1,4-dioxane, DMSO, THF, 1,4-dioxane/water or THF/water;

a volume ratio of 1,4-dioxane or THF to water in said solvent b is 3~6:1;

a catalyst is selected from Pd(dppf)Cl$_2$, or Pd(PPh$_3$)$_4$;

2-dimethylaminoethyl chloride or 2-dimethylaminoethyl bromide can be in the form of its salt.

17. A compound represented by the following formula, as intermediates for preparation of Compound 1,

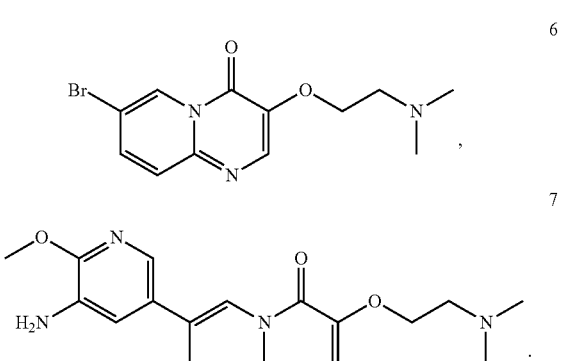

* * * * *